(12) United States Patent
Nakao

(10) Patent No.: US 12,129,240 B2
(45) Date of Patent: Oct. 29, 2024

(54) SULFONIUM SALT, PHOTOACID GENERATOR, CURABLE COMPOSITION AND RESIST COMPOSITION

(71) Applicant: SAN-APRO LTD., Kyoto (JP)

(72) Inventor: Takuto Nakao, Kyoto (JP)

(73) Assignee: SAN-APRO LTD., Kyoto (JP)

( * ) Notice: Subject to any disclaimer, the term of this patent is extended or adjusted under 35 U.S.C. 154(b) by 579 days.

(21) Appl. No.: 17/419,504

(22) PCT Filed: Dec. 16, 2019

(86) PCT No.: PCT/JP2019/049093
§ 371 (c)(1),
(2) Date: Jun. 29, 2021

(87) PCT Pub. No.: WO2020/145043
PCT Pub. Date: Jul. 16, 2020

(65) Prior Publication Data
US 2022/0089562 A1    Mar. 24, 2022

(30) Foreign Application Priority Data

Jan. 10, 2019 (JP) ................................. 2019-002370

(51) Int. Cl.
| | |
|---|---|
| G03F 7/004 | (2006.01) |
| C07D 333/78 | (2006.01) |
| G03F 7/039 | (2006.01) |
| G03F 7/32 | (2006.01) |
| G03F 7/38 | (2006.01) |
| G03F 7/40 | (2006.01) |

(52) U.S. Cl.
CPC ......... *C07D 333/78* (2013.01); *G03F 7/0045* (2013.01); *G03F 7/0392* (2013.01); *G03F 7/322* (2013.01); *G03F 7/38* (2013.01); *G03F 7/40* (2013.01)

(58) Field of Classification Search
CPC ... C07D 333/78; C07D 335/16; G03F 7/0045; G03F 7/0392; G03F 7/322; G03F 7/038; G03F 7/40; G03F 7/004; G03F 7/0397; G03F 7/0382; G03F 7/039; C07C 381/12
See application file for complete search history.

(56) References Cited

U.S. PATENT DOCUMENTS

| | | |
|---|---|---|
| 3,981,897 A | 9/1976 | Crivello |
| 4,058,400 A | 11/1977 | Crivello |
| 4,058,401 A | 11/1977 | Crivello |
| 4,069,055 A | 1/1978 | Crivello |
| 4,069,056 A | 1/1978 | Crivello |
| 4,136,102 A | 1/1979 | Crivello |
| 4,150,988 A | 4/1979 | Crivello |
| 4,161,405 A | 7/1979 | Crivello |
| 4,161,478 A | 7/1979 | Crivello |
| 4,173,551 A | 11/1979 | Crivello |
| 4,175,963 A | 11/1979 | Crivello |
| 4,175,972 A | 11/1979 | Crivello |
| 4,175,973 A | 11/1979 | Crivello |
| 4,192,924 A | 3/1980 | Crivello |
| 4,219,654 A | 8/1980 | Crivello |
| 4,234,732 A | 11/1980 | Crivello |
| 4,250,311 A | 2/1981 | Crivello |
| 4,273,668 A | 6/1981 | Crivello |
| 4,283,312 A | 8/1981 | Crivello |
| 4,329,306 A | 5/1982 | Crivello |
| 4,407,759 A | 10/1983 | Crivello |
| 4,417,061 A | 11/1983 | Crivello |
| 6,093,753 A | 7/2000 | Takahashi |
| 6,723,483 B1 * | 4/2004 | Oono ............ G03F 7/004 430/270.1 |

(Continued)

FOREIGN PATENT DOCUMENTS

| | | |
|---|---|---|
| CN | 101952269 | 1/2011 |
| CN | 104918914 | 9/2015 |

(Continued)

OTHER PUBLICATIONS

Machine translation of WO 2017212963 A1 (Year: 2017).*

(Continued)

*Primary Examiner* — Martin J Angebranndt
(74) *Attorney, Agent, or Firm* — Wenderoth, Lind & Ponack, L.L.P.

(57) ABSTRACT

Provided are a novel sulfonium salt having high photosensitivity to g-rays or h-rays; a novel photoacid generator containing a sulfonium salt that has high photosensitivity to g-rays or h-rays, has high solubility in solvents and cationically polymerizable compounds such as epoxy compounds, and has an excellent storage stability in compositions containing the cationically polymerizable compounds; and the like. The present invention relates to a sulfonium salt represented by the formula (1), a photoacid generator containing the sulfonium salt, and the like.

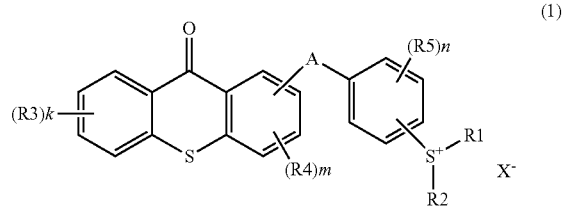

(1)

16 Claims, No Drawings

(56) References Cited

U.S. PATENT DOCUMENTS

| | | | |
|---|---|---|---|
| 9,268,222 B2* | 2/2016 | Takahashi | G03F 7/004 430/18 |
| 2003/0207201 A1* | 11/2003 | Hatakeyama | G03F 7/038 430/270.1 |
| 2003/0235779 A1* | 12/2003 | Hatakeyama | G03C 1/492 430/270.1 |
| 2010/0297540 A1 | 11/2010 | Hayoz et al. | |
| 2011/0039205 A1* | 2/2011 | Suzuki | G03F 7/004 430/270.1 |
| 2011/0300482 A1* | 12/2011 | Suzuki | G03F 7/004 430/270.1 |
| 2018/0143534 A1* | 5/2018 | Takahashi | G03F 7/038 |
| 2019/0300476 A1 | 10/2019 | Fukunaga et al. | |

FOREIGN PATENT DOCUMENTS

| | | | |
|---|---|---|---|
| CN | 107229185 | 10/2017 | |
| JP | 50-151997 | 12/1975 | |
| JP | 2-178303 | 7/1990 | |
| JP | 8-165290 | 6/1996 | |
| JP | 9-118663 | 5/1997 | |
| JP | 2009-269849 | 11/2009 | |
| JP | 2013-178492 | 9/2013 | |
| JP | WO2017212963 A1 * | 12/2017 | C07C 381/12 |
| JP | WO2018003470 A1 * | 1/2018 | C07C 381/12 |
| WO | 2009/136482 | 11/2009 | |
| WO | 2010/095385 | 8/2010 | |
| WO | 2018/003470 | 1/2018 | |

OTHER PUBLICATIONS

Machine translation of Fukunaga et al. WO 2018003470 (2018).*
International Search Report issued Feb. 18, 2020 in International (PCT) Application No. PCT/JP2019/049093.

* cited by examiner

SULFONIUM SALT, PHOTOACID GENERATOR, CURABLE COMPOSITION AND RESIST COMPOSITION

TECHNICAL FIELD

A first aspect of the present invention relates to a sulfonium salt. A second aspect of the present invention relates to a photoacid generator, specifically, a photoacid generator containing a specific sulfonium salt suitable for curing cationically polymerizable compounds by the action of an active energy ray such as light, electron beam, or X-rays. A third aspect of the present invention relates to a curable composition containing the photoacid generator and a cured product obtainable by curing the composition. A fourth aspect of the present invention relates to a chemically amplifiable positive photoresist composition containing the photoacid generator and a method for producing a resist pattern using the chemically amplifiable positive photoresist composition. A fifth aspect of the present invention relates to a chemically amplifiable negative photoresist composition containing the photoacid generator and a cured product obtainable by curing the chemically amplifiable negative photoresist composition.

BACKGROUND ART

Photoacid generator is a general term for compounds which are decomposed when exposed to active energy rays, such as light, electron beam, or X-rays, thereby generating acids. The acids generated by exposure to active energy rays are used as active species in various reactions including polymerization, crosslinking, and deprotection.

Specific examples of the use include the polymerization of cationically polymerizable compounds in the fields of paints, adhesion, and coating, and photolithography (crosslinking in the presence of phenolic resin and crosslinking agents, and acid-catalyzed deprotection of polymers obtained by introducing protecting groups in alkali-soluble resin) to produce electronic parts or to form semiconductor elements.

Medium-pressure or high-pressure mercury lamps are most commonly used as the light source. LED lamps are increasingly used these days to take advantage of the energy-saving properties and long life. In particular, LEDs having an emission wavelength in the h-ray wavelength range (405 nm) are often used because they are available at relatively low prices and have good emission intensities.

Triarylsulfonium salts (Patent Literature 1), phenacylsulfonium salts having naphthalene skeletons (Patent Literature 2), and dialkylbenzylsulfonium salts (Patent Literature 3) have low sensitivity to h-rays among existing photoacid generators. To increase the sensitivity requires the addition of sensitizers. The present inventors have proposed a triarylsulfonium salt (Patent Literature 4). The photosensitivity of the salt to h-rays, g-rays (436 nm), and visible light is enhanced without adding sensitizers. Unfortunately, the salt still has insufficient sensitivity to the rays or light and also has low solubility. The use of the salt is thus limited.

CITATION LIST

Patent Literature

Patent Literature 1: JP S50-151997 A
Patent Literature 2: JP H9-118663 A
Patent Literature 3: JP H2-178303 A
Patent Literature 4: JP 2009-269849 A

SUMMARY OF INVENTION

Technical Problem

In view of the background, a first aim of the present invention is to provide a novel sulfonium salt having high photosensitivity to g-rays or h-rays.

A second aim of the present invention is to provide a novel photoacid generator containing a sulfonium salt, which has high photosensitivity to g-rays or h-rays, has high compatibility with cationically polymerizable compounds such as epoxy compounds, and has an excellent storage stability in compositions containing the photoacid generator and cationically polymerizable compounds such as epoxy compounds.

A third aim of the present invention is to provide an energy ray-curable composition and a cured product, which are provided using the photoacid generator.

A fourth aim of the present invention is to provide a chemically amplifiable positive photoresist composition and a production method thereof, which are provided using the photoacid generator.

A fifth aim of the present invention is to provide a chemically amplifiable negative photoresist composition and a cured product thereof, which are provided using the photoacid generator.

Solution to Problem

The present inventors synthesized a sulfonium salt represented by the following formula (1) and found that the sulfonium salt was suitable for the above-mentioned aims.

Specifically, the present invention provides a sulfonium salt represented by the following formula (1):

[Chem. 1]

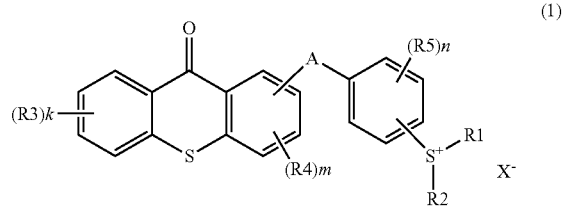

(1)

wherein $R_1$ and $R_2$ each represent a C6-C30 aryl group, a C4-C30 heterocyclic hydrocarbon group, or a C1-C30 alkyl group, one or some of hydrogen atoms in the aryl group, the heterocyclic hydrocarbon group, or the alkyl group are optionally replaced by a substituent (t), the substituent (t) is at least one selected from the group consisting of C1-C18 alkyl groups, hydroxy groups, C1-C18 alkoxy groups, C2-C18 alkylcarbonyl groups, C7-C11 arylcarbonyl groups, C2-C19 acyloxy groups, C6-C20 arylthio groups, C1-C18 alkylthio groups, C6-C10 aryl groups, C4-C20 heterocyclic hydrocarbon groups, C6-C10 aryloxy groups, hydroxy (poly)alkyleneoxy groups represented by HO(-AO)q- (wherein AO represents at least one of an ethyleneoxy group or a propyleneoxy group, and q represents an integer of 1 to 5), and halogen atoms; $R_3$ to $R_5$ each represent an alkyl group, a hydroxy group, an alkoxy group, an alkylcarbonyl group, an arylcarbonyl group, an acyloxy group, an arylthio group, an alkylthio group, an aryl group, a heterocyclic hydrocarbon group, an aryloxy group, a hydroxy (poly) alkyleneoxy group, or a halogen atom; k, m, and n respectively represent the numbers of R3, R4, and R5; k represents an integer of 0 to 4; m represents an integer of 0 to 3; n represents an integer of 1 to 4; A represents a —S— group, a —O— group, a —SO— group, a —SO₂— group, or a —CO— group; O represents an oxygen atom; S represents a sulfur atom; and X⁻ represents a monovalent polyatomic anion.

The present invention also provides a photoacid generator containing the sulfonium salt.

The present invention also provides an energy ray-curable composition containing the photoacid generator and a cationically polymerizable compound.

Furthermore, the present invention provides a cured product obtainable by curing the energy ray-curable composition.

Furthermore, the present invention provides a chemically amplifiable positive photoresist composition containing the photoacid generator and a component (B) that is a resin whose solubility in alkali is increased by the action of an acid.

Furthermore, the present invention provides a method for producing a resist pattern, the method including: stacking a photoresist layer including the chemically amplifiable positive photoresist composition and having a thickness of 5 to 150 μm to form a photoresist laminate; exposing site-selectively the photoresist laminate to light or radiation; and developing the photoresist laminate after the exposure to give a resist pattern.

Furthermore, the present invention provides a chemically amplifiable negative photoresist composition containing: the photoacid generator; a component (F) that is an alkali soluble resin having a phenolic hydroxy group; and a crosslinking agent (G).

Furthermore, the present invention provides a cured product obtainable by curing any of the above chemically amplifiable negative photoresist compositions.

Advantageous Effects of Invention

The sulfonium salt of the present invention has excellent photosensitivity to an active energy rays such as visible light, ultraviolet light, electron beam, and X-rays, has high compatibility with solvents or cationically polymerizable compounds such as epoxy compounds, and provides excellent storage stability in compositions containing the sulfonium salt and cationically polymerizable compounds such as epoxy compounds.

The photoacid generator of the present invention exhibits an excellent curing ability, caused by the action of ultraviolet light, in particular, g-rays and h-rays, for cationically polymerizable compounds. Thus, the cationically polymerizable compounds can be cured without sensitizers.

The energy ray-curable composition of the present invention, which contains the photoacid generator, can be cured by ultraviolet light. Moreover, the energy ray-curable composition of the present invention has high storage stability and does not need sensitizers. Thus, the composition is excellent in cost effectiveness and workability.

The cured product of the present invention is obtainable without sensitizers. Thus, the cured product does not suffer coloring or degradation caused by sensitizer residues.

The chemically amplifiable positive photoresist composition and the chemically amplifiable negative photoresist composition of the present invention, which contain the photoacid generator, can form a resist having high sensitivity to g-rays and h-rays (i.e., enable pattern formation with a lower exposure than conventional ones). Furthermore, the chemically amplifiable positive photoresist composition and the chemically amplifiable negative photoresist composition of the present invention have high storage stability and form good resist patterns.

DESCRIPTION OF EMBODIMENTS

Embodiments of the present invention are described in detail below.

The sulfonium salt of the present invention is represented by the following formula (1).

[Chem. 2]

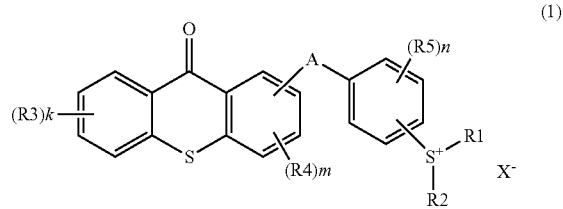

(1)

Examples of the alkyl group for any of R3 to R5 in the formula (1) include C1-C18 linear alkyl groups (e.g., methyl, ethyl, n-propyl, n-butyl, n-pentyl, n-octyl, n-decyl, n-dodecyl, n-tetradecyl, n-hexadecyl, and n-octadecyl), C1-C18 branched alkyl groups (e.g., isopropyl, isobutyl, sec-butyl, tert-butyl, isopentyl, neopentyl, tert-pentyl, isohexyl, and isooctadecyl), and C3-C18 cycloalkyl groups (e.g., cyclopropyl, cyclobutyl, cyclopentyl, cyclohexyl, and 4-decylcyclohexyl).

Examples of the alkoxy group for any of R3 to R5 include C1-C18 linear or branched alkoxy groups (e.g., methoxy, ethoxy, propoxy, isopropoxy, butoxy, isobutoxy, sec-butoxy, tert-butoxy, hexyloxy, decyloxy, dodecyloxy, and octadecyloxy).

Examples of the alkylcarbonyl group for any of R3 to R5 include C2-C18 linear or branched alkylcarbonyl groups (e.g., acetyl, propionyl, butanoyl, 2-methylpropionyl, heptanoyl, 2-methylbutanoyl, 3-methylbutanoyl, octanoyl, decanoyl, dodecanoyl, and octadecanoyl).

Examples of the arylcarbonyl group for any of R3 to R5 include C7-C11 arylcarbonyl groups (e.g., benzoyl and naphthoyl).

Examples of the acyloxy group for any of R3 to R5 include C2-C19 linear or branched acyloxy groups (e.g., acetoxy, ethylcarbonyloxy, propylcarbonyloxy, isopropylcarbonyloxy, butylcarbonyloxy, isobutylcarbonyloxy, sec-butylcarbonyloxy, tert-butylcarbonyloxy, octylcarbonyloxy, tetradecylcarbonyloxy, and octadecylcarbonyloxy).

Examples of the arylthio group for any of R3 to R5 include C6-C20 arylthio groups (e.g., phenylthio, 2-methylphenylthio, 3-methylphenylthio, 4-methylphenylthio, 2-chlorophenylthio, 3-chlorophenylthio, 4-chlorophenylthio, 2-bromophenylthio, 3-bromophenylthio, 4-bromophenylthio, 2-fluorophenylthio, 3-fluorophenylthio, 4-fluorophenylthio, 2-hydroxyphenylthio, 4-hydroxyphenylthio, 2-methoxyphenylthio, 4-methoxyphenylthio, 1-naphthylthio, 2-naphthylthio, 4-[4-(phenylthio)benzoyl]phenylthio, 4-[4-(phenylthio)phenoxy]phenylthio, 4-[4-(phenylthio)phenyl]phenylthio, 4-(phenylthio)phenylthio, 4-benzoylphenylthio, 4-benzoyl-2-chlorophenylthio, 4-benzoyl-3-chlorophenylthio, 4-benzoyl-3-methylthio phenylthio, 4-benzoyl-2-methylthio phenylthio, 4-(4-methylthiobenzoyl)phenylthio, 4-(2-methylthiobenzoyl)phenylthio, 4-(p-methylbenzoyl)phenylthio, 4-(p-ethylbenzoyl)phenylthio, 4-(p-isopropylbenzoyl)phenylthio, and 4-(p-tert-butylbenzoyl)phenylthio).

Examples of the alkylthio group for any of R3 to R5 include C1-C18 linear or branched alkylthio groups (e.g., methylthio, ethylthio, propylthio, isopropylthio, butylthio, isobutylthio, sec-butylthio, tert-butylthio, pentylthio, isopentylthio, neopentylthio, tert-pentylthio, octylthio, decylthio, dodecylthio, and isooctadecylthio).

Examples of the aryl group for any of R3 to R5 include C6-C10 aryl groups (e.g., phenyl, tolyl, dimethylphenyl, and naphthyl).

Examples of the heterocyclic hydrocarbon group for any of R3 to R5 include C4-C20 heterocyclic hydrocarbon groups (e.g., thienyl, furanyl, pyranyl, pyrrolyl, oxazolyl, thiazolyl, pyridyl, pyrimidyl, pyrazinyl, indolyl, benzofuranyl, benzothienyl, quinolyl, isoquinolyl, quinoxalinyl, quinazolinyl, carbazolyl, acridinyl, phenothiazinyl, phenazinyl, xanthenyl, thianthrenyl, phenoxazinyl, phenoxathiinyl, chromanyl, isochromanyl, dibenzothienyl, xanthonyl, thioxanthonyl, and dibenzofuranyl).

Examples of the aryloxy group for any of R3 to R5 include C6-C10 aryloxy groups (e.g., phenoxy and naphthyloxy).

Examples of the hydroxy (poly)alkyleneoxy group for any of R3 to R5 include hydroxy (poly)alkyleneoxy groups represented by the following formula (2):

HO(-AO)q-     (2)

wherein AO represents an ethyleneoxy group and/or a propyleneoxy group, and q represents an integer of 1 to 5.

Examples of the halogen atom for any of R3 to R5 include a fluorine atom, a chlorine atom, a bromine atom, and an iodine atom.

R3 to R5 may be the same as or different from one another or some of them may be different from one another.

The symbol k represents the number of R3 and represents an integer of 0 to 4, preferably 0 to 2, still more preferably 0 or 1, particularly preferably 0. The symbol m represents the number of R4 and represents an integer of 0 to 3, preferably 0 or 1, particularly preferably 0. The symbol n represents the number of R5 and represents an integer of 1 to 4, preferably 1 or 2 from the standpoint of the availability of industrial materials, particularly preferably 2 from the standpoint of solubility.

The bonding position of R5 is not limited. When the bonding is at a position ortho to a C—S$^+$ bond, the sulfonium salt has better photosensitivity.

In the formula (1), A represents a —O— group, a —S— group, a —SO— group, a —SO$_2$— group, or a —CO— group, preferably a —S— group.

In the formula (1), R1 and R2 are each selected from a C6-C30 aryl group, a C4-C30 heterocyclic hydrocarbon group, or C1-C30 alkyl group. One or some of hydrogen atoms in the aryl group, the heterocyclic hydrocarbon group, or the alkyl group are optionally replaced by a substituent (t).

The substituent (t) includes at least one selected from the group consisting of C1-C18 alkyl groups, hydroxy groups, C1-C18 alkoxy groups, C2-C18 alkylcarbonyl groups, C7-C11 arylcarbonyl groups, C2-C19 acyloxy groups, C6-C20 arylthio groups, C1-C18 alkylthio groups, C6-C10 aryl groups, C4-C20 heterocyclic hydrocarbon groups, C6-C10 aryloxy groups, hydroxy (poly)alkyleneoxy groups, and halogen atoms. The substituent (t) is the same as the substituent described for R3 to R5.

Examples of the C6-C30 aryl group for any of R1 and R2 include a monocyclic aryl group and a condensed polycyclic aryl group.

Examples of the monocyclic aryl group include phenyl, hydroxyphenyl, toluyl, dimethylphenyl, trimethylphenyl, ethylphenyl, diethylphenyl, triethylphenyl, n-propylphenyl, isopropylphenyl, n-butylphenyl, isobutylphenyl, sec-butylphenyl, tert-butylphenyl, methoxyphenyl, ethoxyphenyl, n-propoxyphenyl, isopropoxyphenyl, n-butoxyphenyl, isobutoxyphenyl, sec-butoxyphenyl, tert-butoxyphenyl, acetylphenyl, benzoylphenyl, naphthoylphenyl, phenylthiophenyl, naphthylthiophenyl, biphenylyl, phenoxyphenyl, naphthoxyphenyl, nitrophenyl, fluorophenyl, chlorophenyl, and bromophenyl.

Examples of the condensed polycyclic aryl group include naphthyl, anthracenyl, phenanthrenyl, pyrenyl, chrysenyl, naphthacenyl, benzoanthracenyl, anthraquinolyl, fluorenyl, naphthoquinolyl, hydroxynaphthyl, methylnaphthyl, ethylnaphthyl, methoxynaphthyl, ethoxynaphthyi, acetylnaphthyl, benzoylnaphthyl, phenylthionaphthyl, phenylnaphthyl, phenoxynaphthyl, nitronaphthyl, fluoronaphthyl, chloronaphthyl, bromonaphthyl, hydroxyanthracenyl, methylanthracenyl, ethylanthracenyl, methoxyanthracenyl, ethoxyanthracenyl, acetylanthracenyl, benzoylanthracenyl, phenylthioanthracenyl, phenoxyanthracenyl, nitroanthracenyl, fluoroanthracenyl, chloroanthracenyl, and bromoanthracenyl.

Examples of the C4-C30 heterocyclic hydrocarbon group for any of R1 and R2 include cyclic hydrocarbon groups each having one to three heteroatoms (e.g., oxygen atom, nitrogen atom, and sulfur atom) in the ring. Examples also include monocyclic heterocyclic hydrocarbon groups and condensed polycyclic heterocyclic hydrocarbon groups.

Examples of the monocyclic heterocyclic hydrocarbon groups include thienyl, furanyl, pyranyl, pyrrolyl, oxazolyl, thiazolyl, pyridyl, pyrimidyl, pyrazinyl, hydroxythienyl, methylthienyl, ethylthienyl, methoxythienyl, acetylthienyl, benzoylthienyl, phenylthiothienyl, phenoxythienyl, nitrothienyl, fluorothienyl, chiorothienyl, bromothienyl, hydroxyfuranyl, methylfuranyl, ethylfuranyl, methoxyfuranyl, acetylfuranyl, benzoylfuranyl, phenylthiofuranyl, phenoxyfuranyl, nitrofuranyl, fluorofuranyl, chlorofuranyl, and bromofuranyl.

Examples of the condensed polycyclic heterocyclic hydrocarbon groups include indolyl, benzofuranyl, isobenzofuranyl, benzothienyl, isobenzothienyl, quinolyl, isoquinolyl, quinoxalinyl, quinazolinyl, carbazolyl, acridinyl, phenothiazinyl, phenazinyl, xanthenyl, thianthrenyl, phenoxazinyl, phenoxathiinyl, chromanyl, isochromanyl, dibenzothienyl, xanthonyl, thioxanthonyl, dibenzofuranyl, hydroxyxanthenyl, methylxanthenyl, ethylxanthenyl, methoxyxanthenyl, acetylxanthenyl, benzoylxanthenyl, phenylthioxanthenyl, phenoxyxanthenyl, nitroxanthenyl, fluoroxanthenyl, chioroxanthenyl, bromoxanthenyl, hydroxythianthrenyl, methylthianthrenyl, ethylthianthrenyl, methoxythianthrenyl, benzoylthianthrenyl, phenylthiothianthrenyl, phenoxythianthrenyl, nitrothianthrenyl, fluorothianthrenyl, chiorothianthrenyl, bromothianthrenyl, hydroxyxanthonyl, methylxanthonyl, dimethylxanthonyl, ethylxanthonyl, diethylxanthonyl, n-propylxanthonyl, isopropylxanthonyl, methoxyxanthonyl, acetylxanthonyl, benzoylxanthonyl, phenylthioxanthonyl, phenoxyxanthonyl, acetoxyxanthonyl, nitroxanthonyl, fluoroxanthonyl, chloroxanthonyl, hydroxythioxanthonyl, methylthioxanthonyl, dimethylthioxanthonyl, ethylthioxanthonyl, diethylthioxanthonyl, n-propylthioxanthonyl, isopropylthioxanthonyl, methoxythioxanthonyl, acetylthioxanthonyl, benzoylthioxanthonyl, phenylthiothioxanthonyl, phenoxythioxanthonyl, acetoxythioxanthonyl, nitrothioxanthonyl, fluorothioxanthonyl, chlorothioxanthonyl, and bromothioxanthonyl.

Examples of the C1-C30 alkyl group for any of R1 and R2 include linear alkyl groups (e.g., methyl, ethyl, propyl, butyl, pentyl, octyl, decyl, dodecyl, tetradecyl, hexadecyl, octadecyl, benzyl, diphenylmethyl, naphthylmethyl, anthracenylmethyl, phenacyl (—$CH_2COC_6H_5$), naphthoylmethyl, and anthoylmethyl), branched alkyl groups (e.g., isopropyl, isobutyl, sec-butyl, tert-butyl, isopentyl, neopentyl, tert-pentyl, and isohexyl), and cycloalkyl groups (e.g., cyclopropyl, cyclobutyl, cyclopentyl, and cyclohexyl).

Preferably, R1 and R2 each represent a C6-C30 aryl group in which one or some of hydrogen atoms are optionally replaced by a substituent (t) or a C4-C30 heterocyclic hydrocarbon group in which one or some of hydrogen atoms are optionally replaced by a substituent (t). More preferably, at least one of R1 or R2 represents a C4-C30 heterocyclic hydrocarbon group. Particularly preferably, R1 represents a thioxanthonyl group and R2 represents a C6-C30 aryl group optionally substituted with a substituent (t) from the standpoint of photosensitivity and solubility.

The substituent (t) is preferably a C1-C18 alkyl group, a hydroxy group, a C1-C18 alkoxy group, a C2-C18 alkylcarbonyl group, or a C7-C11 arylcarbonyl group, more preferably an alkyl group or an alkoxy group, particularly preferably a methyl group, an ethyl group, a propyl group (n-propyl, isopropyl), a butyl group (n-butyl, isobutyl, sec-butyl, tert-butyl), a methoxy group, or an ethoxy group.

In the formula (1), $X^-$ may be any monovalent polyatomic anion and is an anion of an acid (HX) generated by exposing the sulfonium salt of the present invention to an active energy ray (e.g., visible light, ultraviolet light, electron beam, and X-rays). Preferably, it is an anion represented by $MY_a^-$, $(Rf)_bPF_{6-b}^-$, $R^6{}_cBY_{4-c}^-$, $R^6{}_cGaY_{4-c}^-$, $R^7SO_3^-$, $(R^7SO_2)_3C^-$, or $(R^7SO_2)_2N^-$.

M represents a phosphorus atom, a boron atom, or an antimony atom.

Y represents a halogen atom (preferably, fluorine atom).

Rf represents an alkyl group (preferably C1-C8 alkyl group) in which 80 mol % or more of hydrogen atoms are replaced by fluorine atoms. Examples of the alkyl group to be Rf by the replacement with fluorine atoms include linear alkyl groups (e.g., methyl, ethyl, propyl, butyl, pentyl, and octyl), branched alkyl groups (e.g., isopropyl, isobutyl, sec-butyl, and tert-butyl), and cycloalkyl groups (e.g., cyclopropyl, cyclobutyl, cyclopentyl, and cyclohexyl). The ratio, by the number of moles, of hydrogen atoms replaced by fluorine atoms in the alkyl group as Rf to hydrogen atoms in the original alkyl group is preferably 80 mol % or higher, more preferably 90% or higher, particularly preferably 100%. When the ratio of the replacement with fluorine atoms is within the preferred range, the sulfonium salt has better photosensitivity. Particularly preferred examples of Rf include $CF_3$—, $CF_3CF_2$—, $(CF_3)_2CF$—, $CF_3CF_2CF_2$—, $CF_3CF_2CF_2CF_2$—, $(CF_3)_2CFCF_2$—, $CF_3CF_2(CF_3)CF$—, and $(CF_3)_3C$—. The b Rfs are independent from one another and are the same as or different from one another.

P represents a phosphorus atom. F represents a fluorine atom.

$R^6$ represents a phenyl group in which one or some of hydrogen atoms is/are replaced by at least one element or electron-withdrawing group. Examples of the one element include halogen atoms, such as a fluorine atom, a chlorine atom, and a bromine atom. Examples of the electron-withdrawing group include a trifluoromethyl group, a nitro groups, and a cyano group. Preferred among these are phenyl groups in which one hydrogen atom is replaced by a fluorine atom or a trifluoromethyl group. The c $R^6$s are independent from one another and are the same as or different from one another.

B represents a boron atom. Ga represents a gallium atom.

$R^7$ represents a C1-C20 alkyl group, a C1-C20 perfluoroalkyl group, or a C6-C20 aryl group. The alkyl group and the perfluoroalkyl group may each be linear, branched, or cyclic. The aryl group may be unsubstituted or substituted.

S represents a sulfur atom. O represents an oxygen atom. C represents a carbon atom. N represents a nitrogen atom.

The symbol a represents an integer of 4 to 6.

The symbol b represents an integer of preferably 1 to 5, more preferably 2 to 4, particularly preferably 2 or 3.

The symbol c represents an integer of preferably 1 to 4, more preferably 4.

Examples of the anion represented by $MY_a^-$ include anions represented by $SbF_6^-$, $PF_6^-$, and $BF_4^-$.

Examples of the anion represented by $(Rf)_bPF_{6-b}^-$ include anions represented by $(CF_3CF_2)_2PF_4^-$, $(CF_3CF_2)_3PF_3^-$, $((CF_3)_2CF)_2PF_4^-$, $((CF_3)_2CF)_3PF_3^-$, $(CF_3CF_2CF_2)_2PF_4^-$, $(CF_3CF_2CF_2)_3PF_3^-$, $((CF_3)_2CFCF_2)_2PF_4^-$, $((CF_3)_2CFCF_2)_3PF_3^-$, $(CF_3CF_2CF_2CF_2)_2PF_4^-$, and $(CF_3CF_2CF_2CF_2)_3PF_3^-$. Preferred among these are anions represented by $(CF_3CF_2)_3PF_3^-$, $(CF_3CF_2CF_2)_3PF_3^-$, $((CF_3)_2CF)_3PF_3^-$, $((CF_3)_2CF)_2PF_4^-$, $((CF_3)_2CFCF_2)_3PF_3^-$, and $((CF_3)_2CFCF_2)_2PF_4^-$.

Examples of the anion represented by $R^6{}_cBY_{4-c}^-$ include anions represented by $(C_6F_5)_4B^-$, $((CF_3)_2C_6H_3)_4B^-$, $(CF_3C_6H_4)_4B^-$, $(C_6F_5)_2BF_2^-$, $C_6F_5BF_3^-$, and $(C_6H_3F_2)_4B^-$. Preferred among these are anions represented by $(C_6F_5)_4B^-$ and $((CF_3)_2C_6H_3)_4B^-$.

Examples of the anion represented by $R^6{}_cGaY_{4-c}^-$ include anions represented by $(C_6F_5)_4Ga^-$, $((CF_3)_2C_6H_3)_4Ga^-$, $(CF_3C_6H_4)_4Ga^-$, $(C_6F_5)_2GaF_2^-$, $C_6F_5GaF_3^-$, and $(C_6H_3F_2)_4Ga^-$. Preferred among these are anions represented by $(C_6F_5)_4Ga^-$ and $((CF_3)_2C_6H_3)_4Ga^-$.

Examples of the anion represented by $R^7SO_3^-$ include a trifluoromethanesulfonic acid anion, a pentafluoroethanesulfonic acid anion, a heptafluoropropanesulfonic acid anion, a nonafluorobutanesulfonic acid anion, a pentafluorophenyl sulfonic acid anion, a p-toluenesulfonic acid anion, a benzenesulfonic acid anion, a camphor sulfonic acid anion, a methanesulfonic acid anion, an ethanesulfonic acid anion, a propanesulfonic acid anion, and a butanesulfonic acid anion. Preferred among these are trifluoromethanesulfonic acid anion, nonafluorobutanesulfonic acid anion, methanesulfonic acid anion, butanesulfonic acid anion, camphor sulfonic acid anion, benzenesulfonic acid anion, and p-toluenesulfonic acid anion.

Examples of the anion represented by $(R^7SO_2)_3C^-$ include anions represented by $(CF_3SO_2)_3C^-$, $(C_2F_5SO_2)_3C^-$, $(C_3F_7SO_2)_3C^-$, and $(C_4F_9SO_2)_3C^-$.

Examples of the anion represented by $(R^7SO_2)_2N^-$ include anions represented by $(CF_3SO_2)_2N^-$, $(C_2F_5SO_2)_2N^-$, $(C_3F_7SO_2)_2N^-$, and $(C_4F_9SO_2)_2N^-$.

Examples of usable monovalent polyatomic anions other than the anions represented by $MY_a^-$, $(Rf)_bPF_{6-b}^-$, $R^6{}_cBY_{4-c}^-$, $R^6{}_cGaY_{4-c}^-$, $R^7SO_3^-$, $(R^7SO_2)_3C^-$, or $(R^7SO_2)_2N^-$ include perhalogen acid ions (e.g., $ClO_4^-$, $BrO_4^-$), halogenated sulfonic acid ions (e.g., $FSO_3^-$, $ClSO_3^-$), sulfuric acid ions (e.g., $CH_3SO_4^-$, $CF_3SO_4^-$, $HSO_4^-$), carbonate ions (e.g., $HCO_3^-$, $CH_3CO_3^-$), aluminic acid ions (e.g., $AlCl_4^-$, $AlF_4^-$), hexafluorobismuthic acid ions ($BiF_6^-$), carboxylic acid ions ($CH_3COO^-$, $CF_3COO^-$, $C_6H_5COO^-$, $CH_3C_6H_4COO^-$, $C_6F_5COO^-$, $CF_3C_6H_4COO^-$), aryl boric acid ions (e.g., B(C$_6$H$_5$)$_4$$^-$, CH$_3$CH$_2$CH$_2$CH$_2$B(C$_6$H$_5$)$_3$$^-$), thiocyanic acid ions (SCN$^-$), and nitric acid ions (NO$_3$$^-$).

Preferred among the above X$^-$ is an anion represented by MY$_a$$^-$, (Rf)$_b$PF$_{6-b}$$^-$, R$^6$$_c$BY$_{4-c}$$^-$, R$^6$$_c$GaY$_{4-c}$$^-$, R$^7$SO$_3$$^-$, (R$^7$SO$_2$)$_3$C$^-$, or (R$^7$SO$_2$)$_2$N$^-$, more preferably an anion represented by SbF$_6$$^-$, PF$_6$$^-$, (CF$_3$CF$_2$)$_3$PF$_3$$^-$, (C$_6$F$_5$)$_4$B$^-$, ((CF$_3$)$_2$C$_6$H$_3$)$_4$B$^-$, (C$_6$F$_5$)$_4$Ga$^-$, or ((CF$_3$)$_2$C$_6$H$_3$)$_4$Ga$^-$ because it is highly cationically polymerizable. Preferred examples also include anions represented by (CF$_3$CF$_2$)$_3$PF$_3$$^-$, (C$_6$F$_5$)$_4$B$^-$, ((CF$_3$)$_2$C$_6$H$_3$)$_4$B$^-$, (C$_6$F$_5$)$_4$Ga$^-$, and ((CF$_3$)$_2$C$_6$H$_3$)$_4$Ga$^-$, a trifluoromethanesulfonic acid anion, nonafluorobutanesulfonic acid anions, methanesulfonic acid anions, butanesulfonic acid anions, camphor sulfonic acid anions, benzenesulfonic acid anions, p-toluenesulfonic acid anions, and anions represented by (CF$_3$SO$_2$)$_3$C$^-$ and (CF$_3$SO$_2$)$_2$N$^-$ because they provide better resist resolution and better pattern shapes. Particularly preferred examples include anions represented by (CF$_3$CF$_2$)$_3$PF$_3$$^-$, nonafluorobutanesulfonic acid anions, and anions represented by (C$_6$F$_5$)$_4$B$^-$, ((CF$_3$)$_2$C$_6$H$_3$)$_4$B$^-$, and (CF$_3$SO$_2$)$_3$C$^-$ because they have good compatibility with cationically polymerizable compounds and resist compositions. An anion represented by (C$_6$F$_5$)$_4$Ga$^-$ is more preferred because it is excellent in heat resistant transparency.

The sulfonium salt can be produced by the following production method.

<Production Method>

A method represented by the following reaction scheme (for example, the method disclosed in "Jikken Kagaku Koza (Lectures of Experimental Chemistry)" 4th Edition, vol. 24, p. 376, published by Maruzen Co., Ltd. (1992), JP H7-329399 A, JP H8-165290 A, JP H10-212286 A, or JP H10-7680 A).

[Chem. 3]

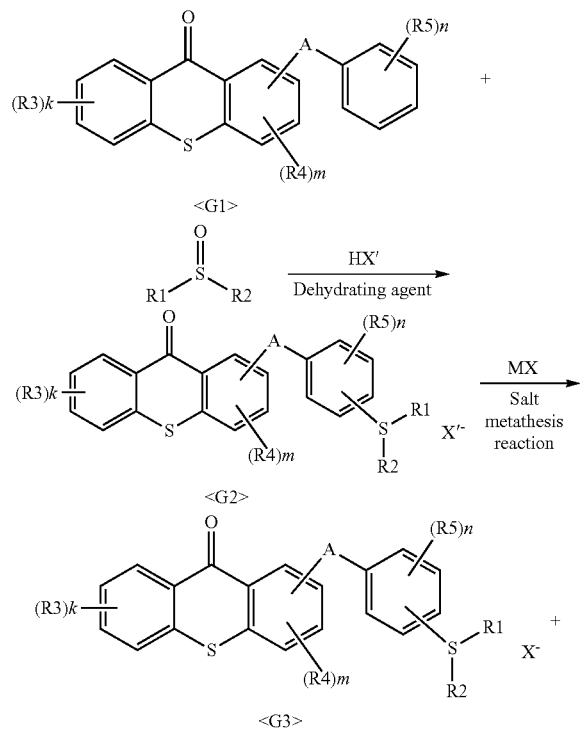

R1 to R5, A, S, O, X$^-$, k, m, and n in the reaction scheme are as defined in the formula (1). H represents a hydrogen atom.

HX' represents a conjugate acid of a monovalent polyatomic anion. From the standpoint of availability, acid stability, and reaction yield, HX' preferably represents a methanesulfonic acid, a perfluoromethanesulfonic acid, or a sulfuric acid.

Examples of the dehydrating agent include phosphoric anhydride, acetic anhydride, and concentrated sulfuric acid.

The monovalent polyatomic anion (X'$^-$) may be replaced by a different anion that is the anion (X$^-$) in the present invention by a salt metathesis reaction shown above, for example.

MX represents a salt of an alkali metal (e.g., lithium, sodium, and potassium) cation and a different anion that is the anion in the present invention (for example, an anion represented by MY$_a$$^-$, (Rf)$_b$PF$_{6-b}$$^-$, R$^6$$_c$BY$_{4-c}$$^-$, R$^6$$_c$GaY$_{4-c}$$^-$, R$^7$SO$_3$$^-$, (R$^7$SO$_2$)$_3$C$^-$, or (R$^7$SO$_2$)$_2$N$^-$).

The first stage of the reaction in the reaction scheme may be performed without a solvent or in an organic solvent (e.g., acetonitrile, tetrahydrofuran, dioxane, ethanol, acetone), if necessary. The reaction temperature is from about 20° C. to about 105° C.

The second stage of the reaction may be performed soon after the first stage of the reaction. Alternatively, isolation (optionally, refinement) of a reaction intermediate (G2) may be performed between the first and second stages. The reaction intermediate (G2) is mixed with an aqueous solution containing a salt (MX) of an alkali metal cation and the anion in the present invention and stirred to carry out the salt metathesis reaction. Then, a precipitated solid is filtered, or a separated oily substance is extracted with an organic solvent and then the organic solvent is removed, whereby the sulfonium salt of the present invention is obtained in the form of solid or viscous fluid. The solid or viscous fluid can be purified by optionally washing it with an appropriate organic solvent, by recrystallization, or by column chromatography.

The chemical structure of the sulfonium salt of the present invention can be identified by a general analysis technique (for example, $^1$H-, $^{11}$B-, $^{13}$C-, $^{19}$F-, or $^{31}$P-nuclear magnetic resonance spectroscopy, infrared absorption spectrometry, and/or elemental analysis).

The photoacid generator of the present invention contains the sulfonium salt represented by the formula (1) and may also contain a different conventionally known photoacid generator.

When a different photoacid generator is contained, the amount (mol %) of the different photoacid generator relative to the total number of moles of the sulfonium salt represented by the formula (1) of the present invention is preferably 0.1 to 100, still more preferably 0.5 to 50.

Examples of the different photoacid generator include conventionally known ones, such as onium salts (e.g., sulfonium, iodonium, selenium, ammonium, and phosphonium) and salts of a transition metal complex ion and an anion.

Before using the photoacid generator of the present invention, it may be dissolved in a solvent that does not inhibit polymerization, crosslinking, deprotection reaction, and the like so that it is easily dissolved in a cationically polymerizable compound or a chemically amplifiable resist composition.

Examples of the solvent include: carbonates such as propylene carbonate, ethylene carbonate, 1,2-butylene carbonate, dimethyl carbonate, and diethyl carbonate; ketones such as acetone, methyl ethyl ketone, cyclohexanone, methyl isoamyl ketone, and 2-heptanone; polyhydric alcohols and derivatives thereof, such as monomethyl ethers, monoethyl ethers, monopropyl ethers, monobutyl ethers, or monophenyl ethers of ethylene glycol, ethylene glycol monoacetate, diethylene glycol, diethylene glycol monoacetate, propylene glycol, propylene glycol monoacetate, dipropylene glycol, and dipropylene glycol monoacetate; cyclic ethers such as dioxane; esters such as ethyl formate, methyl lactate, ethyl lactate, methyl acetate, ethyl acetate, butyl acetate, methyl pyruvate, methyl acetoacetate, ethyl acetoacetate, ethyl pyruvate, ethyl ethoxyacetate, methyl methoxypropionate, ethyl ethoxypropionate, methyl 2-hydroxypropionate, ethyl 2-hydroxypropionate, ethyl 2-hydroxy-2-methylpropionate, methyl 2-hydroxy-3-methylbutanoate, 3-methoxybutyl acetate, 3-methyl-3-methoxybutyl acetate, β-propiolactone, β-butyrolactone, γ-butyrolactone, δ-valerolactone, and ε-caprolactone; and aromatic hydrocarbons such as toluene and xylene.

When a solvent is used, the amount of the solvent is preferably from 15 to 1000 parts by weight, more preferably from 30 to 500 parts by weight per 100 parts by weight of the photoacid generator containing the sulfonium salt of the present invention. A single solvent may be used alone or two or more solvents may be used in combination.

The energy ray-curable composition of the present invention contains the photoacid generator and a cationically polymerizable compound.

Examples of the cationically polymerizable compound as a constituent component of the energy ray-curable composition include cyclic ethers (e.g., epoxide and oxetane), ethylenic unsaturated compounds (e.g., vinyl ether and styrene), bicycloortho esters, spiroortho carbonates, and spiroortho esters (e.g., JP H11-060996 A, JP H09-302269 A, JP 2003-026993 A).

Known epoxides and the like may be used. Examples thereof include aromatic epoxides, alicyclic epoxides, and aliphatic epoxides.

Examples of the aromatic epoxides include glycidyl ethers of monohydric or polyhydric phenols having at least one aromatic ring (e.g., phenol, bisphenol A, phenol novolac, and alkylene oxide adducts thereof).

Examples of the alicyclic epoxides include compounds (e.g., 3,4-epoxycyclohexylmethyl-3,4-epoxycyclohexanecarboxylate) obtained by epoxidation of compounds having at least one cyclohexene or cyclopentene ring with an oxidizing agent.

Examples of the aliphatic epoxides include polyglycidyl ethers of aliphatic polyhydric alcohols or alkylene oxide adducts thereof (e.g., 1,4-butanediol diglycidyl ether, 1,6-hexanediol diglycidyl ether), polyglycidyl esters of aliphatic polybasic acids (e.g., diglycidyl tetrahydrophthalate), and epoxidized long-chain unsaturated compounds (e.g., epoxidized soybean oil and epoxidized polybutadiene).

Known oxetanes and the like may be used. Examples thereof include 3-ethyl-3-hydroxymethyloxetane, 2-ethylhexyl(3-ethyl-3-oxetanylmethyl) ether, 2-hydroxyethyl(3-ethyl-3-oxetanylmethyl) ether, 2-hydroxypropyl(3-ethyl-3-oxetanylmethyl) ether, 1,4-bis[(3-ethyl-3-oxetanylmethoxy)methyl]benzene, oxetanylsilsesquioxane, and phenol novolac oxetane.

Known cationically polymerizable monomers and the like may be used as the ethylenic unsaturated compounds. Examples thereof include aliphatic monovinyl ethers, aromatic monovinyl ethers, polyfunctional vinyl ethers, styrenes, and cationically polymerizable nitrogen-containing monomers.

Examples of the aliphatic monovinyl ethers include methyl vinyl ether, ethyl vinyl ether, butyl vinyl ether, and cyclohexyl vinyl ether.

Examples of the aromatic monovinyl ethers include 2-phenoxyethyl vinyl ether, phenyl vinyl ether, and p-methoxyphenyl vinyl ether.

Examples of the polyfunctional vinyl ethers include butanediol-1,4-divinyl ether and triethylene glycol divinyl ether.

Examples of the styrenes include styrene, α-methylstyrene, p-methoxystyrene, and p-tert-butoxystyrene.

Examples of the cationically polymerizable nitrogen-containing monomers include N-vinylcarbazole and N-vinylpyrrolidone.

Examples of the bicycloortho esters include 1-phenyl-4-ethyl-2,6,7-trioxabicyclo[2.2.2]octane and 1-ethyl-4-hydroxymethyl-2,6,7-trioxabicyclo[2.2.2]octane.

Examples of the spiroortho carbonates include 1,5,7,11-tetraoxaspiro[5.5]undecane and 3,9-dibenzyl-1,5,7,11-tetraoxaspiro[5.5]undecane.

Examples of the spiroortho esters include 1,4,6-trioxaspiro[4.4]nonane, 2-methyl-1,4,6-trioxaspiro[4.4]nonane, and 1,4,6-trioxaspiro[4.5]decane.

Additionally, polyorganosiloxanes having at least one cationically polymerizable group per molecule can be used (those described in JP 2001-348482 A or Journal of Polym. Sci., Part A, Polym. Chem., Vol. 28, 497 (1990), for example).

These polyorganosiloxanes may be any of linear, branched, and cyclic polyorganosiloxanes, or a mixture thereof.

Epoxides, oxetanes, and vinyl ethers are preferred, epoxides and oxetanes are more preferred, and alicyclic epoxides and oxetanes are particularly preferred among the cationically polymerizable compounds. These cationically polymerizable compounds may be used alone or two or more of them may be used in combination.

The amount of the photoacid generator containing the sulfonium salt of the present invention in the energy ray-curable composition is preferably from 0.05 to 20 parts by weight, more preferably from 0.1 to 10 parts by weight per 100 parts by weight of the cationically polymerizable compound. When the amount is within the range, the cationically polymerizable compound is more sufficiently polymerized, so that the resulting cured product obtains better physical properties. The amount is not limited to the above-mentioned range and will be determined taking into account various factors such as the nature of the cationically polymerizable compound, the type and irradiation dose of the energy ray, the temperature, the curing time, the humidity, and the thickness of the film.

The energy ray-curable composition of the present invention may contain known additives (e.g., a sensitizer, a pigment, a filler, an antistatic agent, a flame retardant, a defoaming agent, a fluidity controlling agent, a light stabilizer, an antioxidant, an adhesion imparting agent, an ion scavenger, an anti-coloring agent, a solvent, a nonreactive resin, and a radically polymerizable compound), if necessary.

The sensitizer may be a known sensitizer (e.g., JP H11-279212 A, JP H09-183960 A). Examples thereof include anthracenes (e.g., anthracene, 9,10-dibutoxyanthracene, 9,10-dimethoxyanthracene, 9,10-diethoxyanthracene, 2-ethyl-9,10-dimethoxyanthracene, and 9,10-dipropoxyanthracene); pyrene; 1,2-benzanthracene; perylene; tetracene; coronene; thioxanthones (e.g., thioxanthone, 2-methylthioxanthone, 2-ethylthioxanthone, 2-chlorothioxanthone, 2-isopropylthioxanthone, and 2,4-diethylthioxanthone); phenothiazines (e.g., phenothiazine, N-methylphenothiazine, N-ethylphenothiazine, and N-phenylphenothiazine); xanthone; naphthalenes (e.g., 1-naphthol, 2-naphthol, 1-methoxynaphthalene, 2-methoxynaphthalene, 1,4-dihydroxynaphthalene, and 4-methoxy-1-naphthol); ketones (e.g., dimethoxyacetopohenone, diethoxyacetophenone, 2-hydroxy-2-methyl-1-phenylpropan-1-one, 4'-isopropyl-2-hydroxy-2-methylpropiophenone, and 4-benzoyl-4'-methyldiphenyl sulfide); carbazoles (e.g., N-phenylcarbazole, N-ethylcarbazole, poly-N-vinylcarbazole, and N-glycidylcarbazole); chrysenes (e.g., 1,4-dimethoxychrysene and 1,4-di-α-methylbenzyloxychrysene); and phenanthrenes (e.g., 9-hydroxyphenanthrene, 9-methoxyphenanthrene, 9-hydroxy-10-methoxyphenanthrene, and 9-hydroxy-10-ethoxyphenanthrene).

When a sensitizer is contained, the amount of the sensitizer is preferably from 1 to 300 parts by weight, more preferably from 5 to 200 parts by weight per 100 parts of the photoacid generator of the present invention.

Known pigments and the like may be used. Examples thereof include inorganic pigments (e.g., titanium oxide, iron oxide, and carbon black) and organic pigments (e.g., azo pigments, cyanine pigments, phthalocyanine pigments, and quinacridone pigments).

When a pigment is contained, the amount of the pigment is preferably from 0.5 to 400,000 parts by weight, more preferably from 10 to 150,000 parts by weight per 100 parts of the photoacid generator of the present invention.

Known fillers and the like may be used. Examples thereof include fused silica, crystalline silica, calcium carbonate, aluminum oxide, aluminum hydroxide, zirconium oxide, magnesium carbonate, mica, talc, calcium silicate, and lithium aluminum silicate.

When filler is contained, the amount of the filler is preferably from 50 to 600,000 parts by weight, more preferably 300 to 200,000 parts by weight per 100 parts of the photoacid generator of the present invention.

Known antistatic agents and the like may be used. Examples thereof include nonionic antistatic agents, anionic antistatic agents, cationic antistatic agents, ampholytic antistatic agents, and high molecular weight antistatic agents.

When an antistatic agent is contained, the amount of the antistatic agent is preferably from 0.1 to 20,000 parts by weight, more preferably from 0.6 to 5,000 parts by weight per 100 parts of the photoacid generator of the present invention.

Known flame retardants and the like may be used. Examples thereof include inorganic flame retardants (e.g., antimony trioxide, antimony pentoxide, tin oxide, tin hydroxide, molybdenum oxide, zinc borate, barium metaborate, red phosphorus, aluminum hydroxide, magnesium hydroxide, and calcium aluminate); bromine flame retardants (e.g., tetrabromophthalic anhydride, hexabromobenzene, and decabromobiphenyl ether); and phosphate flame retardants (e.g., tris(tribromophenyl) phosphate).

When a flame retardant is contained, the amount of the flame retardant is preferably from 0.5 to 40,000 parts by weight, more preferably from 5 to 10,000 parts by weight per 100 parts of the photoacid generator of the present invention.

Known defoaming agents and the like may be used. Examples thereof include alcoholic defoaming agents, metallic soap defoaming agents, phosphate defoaming agents, fatty acid ester defoaming agents, polyether defoaming agents, silicone defoaming agents, and mineral oil defoaming agents.

Known fluidity controlling agents and the like may be used. Examples thereof include hydrogenated castor oil, oxidized polyethylene, organic bentonite, colloidal silica, amide wax, metallic soap, and acrylic ester polymers.

Known light stabilizers and the like may be used. Examples thereof include ultraviolet absorbing stabilizers (e.g., benzotriazole, benzophenone, salicylates, cyanoacrylates, and derivatives thereof); radical scavenging stabilizers (e.g., hindered amines); and quenching stabilizers (e.g., nickel complexes}.

Known antioxidants and the like may be used. Examples thereof include phenolic antioxidants (e.g., monophenolic, bisphenolic, and macromolecular phenolic antioxidants), sulfur-based antioxidants, and phosphorus-based antioxidants.

Known adhesion imparting agents and the like may be used. Examples thereof include coupling agents, silane coupling agents, and titanium coupling agents.

Known ion scavengers and the like may be used. Examples thereof include organoaluminum (e.g., alkoxyaluminum and phenoxyaluminum).

Known anti-coloring agents and the like may be used. Generally, antioxidants are effective. Examples thereof include phenolic antioxidants (e.g., monophenolic, bisphenolic, and macromolecular phenolic antioxidants), sulfur-based antioxidants, and phosphorus-based antioxidants. The anti-coloring agents hardly prevent coloring in heat resistant tests performed at high temperature.

When a defoaming agent, a fluidity controlling agent, a light stabilizer, an antioxidant, an adhesion imparting agent, an ion scavenger, or an anti-coloring agent is contained, the amount of each agent is preferably from 0.1 to 20,000 parts by weight, more preferably from 0.5 to 5,000 parts by weight per 100 parts of the photoacid generator of the present invention.

Any solvent that can be used to dissolve the cationically polymerizable compound or to control the viscosity of the energy ray-curable composition may be used as the solvent. Examples thereof include those listed above for the photoacid generator.

When a solvent is contained, the amount of the solvent is preferably from 50 to 2,000,000 parts by weight, more preferably from 200 to 500,000 parts by weight per 100 parts of the photoacid generator of the present invention.

Examples of the nonreactive resin include polyester, polyvinyl acetate, polyvinyl chloride, polybutadiene, polycarbonate, polystyrene, polyvinyl ether, polyvinyl butyral, polybutene, hydrogenated styrene-butadiene block copolymers, copolymers of (meth)acrylic acid esters, and polyurethane. The number average molecular weight of each resin is preferably from 1,000 to 500,000, more preferably from 5,000 to 100,000 (the number average molecular weight is a value measured by a general method such as GPC).

When a nonreactive resin is contained, the amount of the nonreactive resin is preferably from 5 to 400,000 parts by weight, more preferably from 50 to 150,000 parts by weight per 100 parts of the photoacid generator of the present invention.

When a nonreactive resin is contained, the nonreactive resin is preferably dissolved in advance in a solvent so that it is readily dissolved in the cationically polymerizable compound or the like.

Known radically polymerizable compounds and the like may be used, such as those described in "Photopolymer Handbook" edited by The Technical Association of Photopolymers, Japan (1989, Kogyo Chosakai Publishing, Co., Ltd.), "UV/EB Koka Gijutsu" (Technology of UV/EB Curing), edited by Sogo Gijutsu Center (1982, Sogo Gijutsu Center), "UV/EB Koka Zairyo" (UV/EB Curable Materials), edited by RadTech Japan (1992, CMC), and the like. Examples thereof include monofunctional monomers, bifunctional monomers, polyfunctional monomers, epoxy (meth)acrylate, polyester (meth)acrylate, and urethane (meth)acrylate.

When a radically-polymerizable compound is contained, the amount of the radically-polymerizable compound is preferably from 5 to 400,000 parts by weight, more preferably from 50 to 150,000 parts by weight per 100 parts of the photoacid generator of the present invention.

When a radically-polymerizable compound is contained, a radical polymerization initiator initiating polymerization with heat or light is preferably used to radically polymerize the radically polymerizable compound.

Known radical polymerization initiators and the like may be used. Examples thereof include thermal radical polymerization initiators (e.g., organic peroxides, azo compounds) and photoradical polymerization initiators (e.g., acetophenone-based initiators, benzophenone-based initiators, Michler's ketone-based initiators, benzoin-based initiators, thioxanthone-based initiators, acylphosphine-based initiators).

When a radical polymerization initiator is contained, the amount of the radical polymerization initiator is preferably from 0.01 to 20 parts by weight, more preferably from 0.1 to 10 parts by weight per 100 parts of the radically polymerizable compound.

The energy ray-curable composition of the present invention may be prepared by uniformly mixing and dissolving the cationically polymerizable compound, the photoacid generator, and optionally additives at room temperature (about 20° C. to 30° C.) or if necessary under heating (about 40° C. to 90° C.), optionally followed by kneading with a triple-roll mill or the like.

A cured product of the energy ray-curable composition of the present invention can be produced by exposing the composition to an energy ray, thereby curing the composition.

The energy ray may be any energy ray having energy to induce the decomposition of the photoacid generator of the present invention. Preferred examples of the energy ray include energy rays in the ultraviolet to visible light region (wavelength: from about 100 to about 800 nm) irradiated from a low pressure-, medium pressure-, high pressure-, or ultra high pressure-mercury lamp, a metal halide lamp, an LED lamp, a xenon lamp, a carbon arc lamp, a fluorescent lamp, a semiconductor solid-state laser, an argon laser, a He—Cd laser, a KrF excimer laser, an ArF excimer laser, or an $F_2$ laser. Radiations with a high energy, such as electron beam or X-rays, may also be used as the energy ray.

The exposure time to an energy ray is influenced by the intensity of the energy ray or the permeability of the energy ray to the energy ray-curable composition. At room temperature (about 20° C. to 30° C.), exposure for about 0.1 to 10 seconds is enough. If the permeability of the energy ray is low or if the energy ray-curable composition is thick, for example, the time may preferably be extended. Most energy ray-curable compositions are cured by cationic polymerization in 0.1 seconds to several minutes after the exposure to an energy ray. Post-curing may optionally be performed by heating at a temperature of room temperature (about 20° C. to 30° C.) to 200° C. for several seconds to several hours after the exposure to the energy ray.

Specific examples of the use of the energy ray-curable composition of the present invention include paints, coating agents, various coating materials (e.g., hard coats, anti-fouling coating materials, anti-fogging coating materials, anti-corrosion coating materials, optical fibers), back surface treatment agents for adhesive tapes, release coating materials of release sheets (e.g., release papers, release plastic films, release metal foils) for adhesive labels, printing plates, dental materials (dental formulations, dental composites), ink compositions, inkjet ink compositions, positive resists (for formation of connection terminals and wiring patterns in production of electronic components such as circuit boards, CSP, and MEMS elements), resist films, liquid resists, negative resists (e.g., permanent film materials of surface protecting films, interlayer dielectric films, or planarizing films for semiconductor elements and the like), resists for MEMS, positive photosensitive materials, negative photosensitive materials, various adhesives (e.g., various temporary fixing agents for electronic components, adhesives for HDD, adhesives for pick-up lenses, adhesives for functional films for FPD (e.g., polarizing plates, antireflection films)), holographic resins, FPD materials (e.g., color filters, black matrices, partition wall materials, photospacers, ribs, orientation films for liquid crystals, sealing agents for FPD), optical members, molding materials (for building materials, optical components, or lenses), casting materials, putty materials, glass fiber impregnating agents, filling materials, sealing materials, sealants, photosemiconductor (LED) sealing materials, optical waveguide materials, nano-imprint materials, stereolithography materials, and micro-stereolithography materials.

The photoacid generator of the present invention, which can generate a strong acid upon exposure to light, may also be used as a photoacid generator for known chemically amplifiable resist materials (e.g., JP 2003-267968 A, JP 2003-261529 A, JP 2002-193925 A).

Examples of the chemically amplifiable resist materials include (1) a two-component chemically amplifiable positive resist containing, as essential components, a resin that can be made soluble in an alkaline developer by the action of an acid, and a photoacid generator; (2) a three-component chemically amplifiable positive resist containing, as essential components, a resin soluble in an alkaline developer, a dissolution inhibitor that can be made soluble in an alkaline developer by the action of an acid, and a photoacid generator; and (3) a chemically amplifiable negative resist containing, as essential components, a resin soluble in an alkaline developer, a crosslinking agent that can crosslink resin to make the resin insoluble in an alkaline developer when heated in the presence of an acid, and a photoacid generator.

The chemically amplifiable positive photoresist composition of the present invention contains: a component (A) containing the photoacid generator of the present invention that is a compound generating an acid when exposed to light or radiation; and a component (B) that is a resin whose solubility in alkali is increased by the action of an acid.

In the chemically amplifiable positive photoresist composition of the present invention, the component (A) may be used with a conventionally known different photoacid generator. Examples of the different photoacid generator include onium salt compounds, sulfone compounds, sulfonic acid ester compounds, sulfone imide compounds, disulfonyl diazo methane compounds, disulfonyl methane compounds, oxime sulfonate compounds, hydrazine sulfonate compounds, triazine compounds, and nitro benzyl compounds. Examples also include organohalides and disulfones.

The conventionally known different photoacid generator is preferably at least one selected from the group consisting of onium compounds, sulfone imide compounds, diazo methane compounds, and oxime sulfonate compounds.

When the conventionally known different photoacid generator is used in combination, it may be used in any amount. Usually, the amount of the different photoacid generator relative to total 100 parts by weight of the sulfonium salt represented by the formula (1) is from 10 to 900 parts by weight, preferably 25 to 400 parts by weight.

The component (A) content in the solids content of the chemically amplifiable positive photoresist composition is preferably from 0.05 to 5% by weight.

<Resin Component (B) Whose Solubility in Alkali is Increased by the Action of an Acid>

The "resin (B) whose solubility in alkali is increased by the action of an acid" (hereinafter, referred to as "component (B)") in the chemically amplifiable positive photoresist composition of the present invention is a resin selected from the group consisting of a novolac resin (B1), a polyhydroxystyrene resin (B2), and an acrylic resin (B3), or a mixture or a copolymer of these resins.

[Novolac Resin (B1)]

Resins represented by the formula (b1) may be used as the novolac resin (B1).

[Chem. 4]

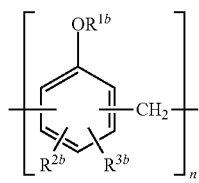

(b1)

In the formula (b1), $R^{1b}$ represents an acid-dissociable, dissolution inhibiting group, $R^{2b}$ and $R^{3b}$ each independently represent a hydrogen atom or a C1-C6 alkyl group, and n represents the number of a repeating unit consisting of a structure in the brackets.

The acid dissociable, dissolution inhibiting group represented by $R^{1b}$ is preferably a C1-C6 linear alkyl group, a C3-C6 branched alkyl group, a C3-C6 cyclic alkyl group, a tetrahydropyranyl group, a tetrahydrofuranyl group, or a trialkylsilyl group.

Specific examples of the acid dissociable, dissolution inhibiting group represented by $R^{1b}$ include methoxyethyl groups, ethoxyethyl groups, n-propoxyethyl groups, isopropoxyethyl groups, n-butoxyethyl groups, isobutoxyethyl groups, tert-butoxyethyl groups, cyclohexyloxyethyl groups, methoxypropyl groups, ethoxypropyl groups, 1-methoxy-1-methylethyl groups, 1-ethoxy-1-methylethyl groups, tert-butoxycarbonyl groups, tert-butoxycarbonylmethyl groups, trimethylsilyl groups, and tri-tert-butyldimethylsilyl groups.

[Polyhydroxystyrene Resin (B2)]

Resins represented by the following formula (b4) may be used as the polyhydroxystyrene resin (B2).

[Chem. 5]

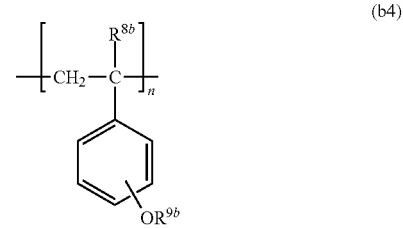

(b4)

In the formula (b4), $R^{8b}$ represents a hydrogen atom or a C1-C6 alkyl group, $R^{9b}$ represents an acid-dissociable, dissolution inhibiting group, and n represents the number of a repeating unit consisting of a structure in the brackets.

The C1-C6 alkyl group is a C1-C6 linear alkyl group, a C3-C6 branched alkyl group, or a C3-C6 cyclic alkyl group. Examples thereof include methyl groups, ethyl groups, propyl groups, isopropyl groups, n-butyl groups, isobutyl groups, tert-butyl groups, pentyl groups, isopentyl groups, and neopentyl groups. Examples of the cyclic alkyl group include cyclopentyl groups and cyclohexyl groups.

Examples of the acid-dissociable, dissolution inhibiting group represented by $R^{9b}$ include the acid dissociable, dissolution inhibiting groups listed as examples for $R^{1b}$.

The polyhydroxystyrene resin (B2) may optionally contain other polymerizable compounds as structural units to appropriately control the physical and chemical properties. The polymerizable compounds may be known radically polymerizable compounds or anionically polymerizable compounds. Examples thereof include: monocarboxylic acids, such as acrylic acid; dicarboxylic acids, such as maleic acid, fumaric acid, and itaconic acid; methacrylic acid derivatives having a carboxyl group and an ester bond, such as 2-methacryloyloxyethyl succinic acid; (meth)acrylic acid alkyl esters, such as methyl (meth)acrylate; (meth)acrylic acid hydroxyalkyl esters, such as 2-hydroxyethyl (meth)acrylate; dicarboxylic acid diesters, such as diethyl maleate; vinyl group-containing aromatic compounds, such as styrene and vinyl toluene; vinyl group-containing aliphatic compounds, such as vinyl acetate; conjugated diolefins, such as butadiene and isoprene; nitrile group-containing polymerizable compounds, such as acrylonitrile; chlorine-containing polymerizable compounds, such as vinyl chloride; and amide bond-containing polymerizable compounds, such as acrylamide.

[Acrylic Resin (B3)]

Resins represented by the following formulas (b5) to (b10) may be used as the acrylic resin (B3).

[Chem. 6]

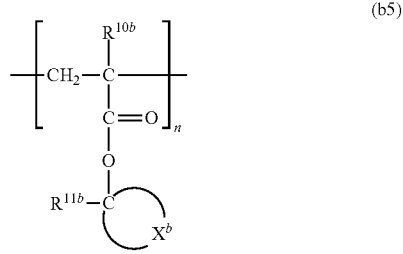

(b5)

(b6)

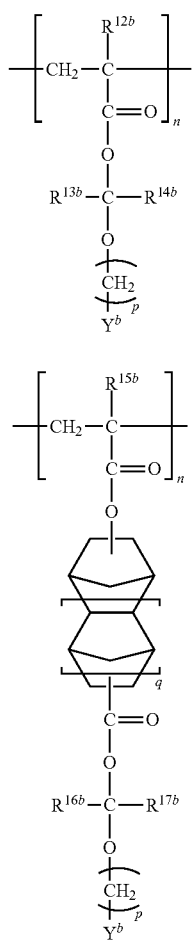

[Chem. 7]

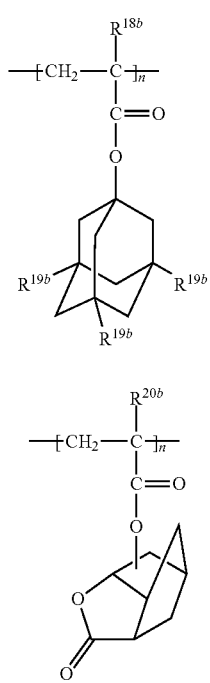

(b7)

(b8)

(b9)

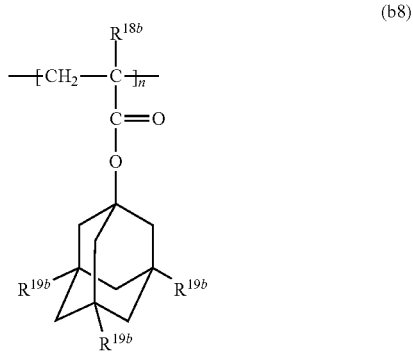

(b10)

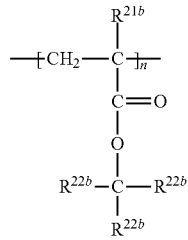

In the formulas (b5) to (b7), $R^{10b}$ to $R^{17b}$ each independently represent a hydrogen atom, a C1-C6 linear alkyl group, a C3-C6 branched alkyl group, a fluorine atom, a fluorinated C1-C6 linear alkyl group, or a fluorinated C3-C6 branched alkyl group; $X^b$, together with a carbon atom to which it is bound, forms a C5-C20 hydrocarbon ring; $Y^b$ represents an optionally substituted aliphatic ring group or an alkyl group; n represents the number of a repeating unit consisting of a structure in the brackets; p represents an integer of 0 to 4, and q represents 0 or 1.

In the formula (b8), the formula (b9), and the formula (b10), $R^{18b}$, $R^{20b}$, and $R^{21b}$ each independently represent a hydrogen atom or a methyl group. In the formula (b8), $R^{19b}$ each independently represents a hydrogen atom, a hydroxyl group, a cyano group, or a COOR$^{23b}$ group ($R^{23b}$ represents a hydrogen atom, a C1-C4 linear alkyl group, a C3-C4 branched alkyl group, or a C3-C20 cycloalkyl group). In the formula (b10), $R^{22b}$s each independently represent a C4-C20 monovalent alicyclic hydrocarbon group or a derivative thereof, a C1-C4 linear alkyl group, or a C3-C4 branched alkyl group. At least one $R^{22b}$ is the alicyclic hydrocarbon group or a derivative thereof, or alternatively, two of $R^{22b}$s, together with a carbon atom to which both of them are bound, form a C4-C20 divalent alicyclic hydrocarbon group or a derivative thereof. The remaining $R^{22b}$(s) each represent a C1-C4 linear alkyl group, a C3-C4 branched alkyl group, or a C4-C20 monovalent alicyclic hydrocarbon group or a derivative thereof.

The acrylic resin (B3) is preferably used as the component (B).

The component (B) has a polystyrene-equivalent weight average molecular weight of preferably 10,000 to 600,000, more preferably 50,000 to 600,000, still more preferably 230,000 to 550,000. When the component (B) has the above-mentioned weight average molecular weight, a resist with excellent resin physical properties may be obtained.

Moreover, the component (B) is preferably a resin having a dispersibility of 1.05 or higher. Herein, the term "dispersibility" is a quotient of the weight average molecular weight divided by the number average molecular weight. When the component (B) has the above-mentioned dispersibility, a resist with excellent plating resistance and excellent resin physical properties may be obtained.

The component (B) content in the solids content of the chemically amplifiable positive photoresist composition is preferably from 5 to 60% by weight.

<Alkali Soluble Resin (C)>

The chemically amplifiable positive photoresist composition of the present invention preferably further contains an alkali soluble resin (hereinafter, referred to as "component (C)") to improve the resin physical properties of a resist. The component (C) is preferably at least one selected from the group consisting of a novolac resin, a polyhydroxystyrene resin, an acrylic resin, and a polyvinyl resin.

The amount of the component (C) per 100 parts by weight of the component (B) is preferably from 5 to 95 parts by weight, more preferably from 10 to 90 parts by weight. When the amount is 5 parts by weight or more, the resin physical properties of a resist can be improved. When the amount is 95 parts by weight or less, film loss during development tends to be prevented.

<Acid Diffusion Control Agent (D)>

The chemically amplifiable positive photoresist composition of the present invention preferably further contains an acid diffusion control agent (D) (hereinafter, referred to as "component (D)") to improve resist pattern shapes, post-exposure delay stability, and the like. The component (D) is preferably a nitrogen-containing compound. The component (D) may optionally contain an organic carboxylic acid or a phosphorous oxo acid, or a derivative thereof.

The chemically amplifiable positive photoresist composition of the present invention may further contain an adhesion assisting agent to enhance the adhesion with a substrate. The adhesion assisting agent is preferably a functional silane coupling agent.

The chemically amplifiable positive photoresist composition of the present invention may further contain a surfactant to improve coatability, defoaming properties, leveling properties, and the like.

The chemically amplifiable positive photoresist composition of the present invention may further contain an acid, an acid anhydride, or a high boiling point solvent for fine adjustment of the solubility in an alkaline developer.

The chemically amplifiable positive photoresist composition of the present invention basically does not need a sensitizer. If necessary, it may contain a sensitizer to supply sensitivity. The sensitizer may be a conventionally known one, and specific examples thereof include those mentioned above.

The amount of the sensitizer relative to total 100 parts by weight of the sulfonium salt represented by the formula (1) is from 5 to 500 parts by weight, preferably from 10 to 300 parts by weight.

An organic solvent may be appropriately added to the chemically amplifiable positive photoresist composition of the present invention to control the viscosity. Specific examples of the organic solvent include those described above.

The amount of the organic solvent is preferably adjusted to a solid concentration of 30% by weight or higher so that a photoresist layer formed with the chemically amplifiable positive photoresist composition of the present invention (for example, by spin coating) has a thickness of 5 μm or more.

The chemically amplifiable positive photoresist composition of the present invention may be prepared simply by mixing and stirring the components by a usual method, for example. If necessary, a dispersing device such as a dissolver, a homogenizer, or a three-roll mill may be used for dispersion or mixing. The obtained mixture may be filtrated with a mesh or a membrane filter.

The chemically amplifiable positive photoresist composition of the present invention is suitable for forming a photoresist layer having a thickness of usually 5 to 150 μm, more preferably 10 to 120 μm, still more preferably 10 to 100 μm on a support. The resulting photoresist laminate includes a support and a photoresist layer including the chemically amplifiable positive photoresist composition of the present invention stacked on the support.

Any support may be used, including conventionally known ones. Examples thereof include substrates for electronic components and those substrates having prescribed wiring patterns. The substrate may be, for example, a metal substrate from silicon, silicon nitride, titanium, tantalum, palladium, titanium tungsten, copper, chromium, iron, aluminum, or the like or a glass substrate. The chemically amplifiable positive photoresist composition of the present invention can form a resist pattern favorably on a copper substrate. Examples of the material of the wiring pattern include copper, solder, chromium, aluminum, nickel, and gold.

For example, the photoresist laminate may be produced as follows: A solution of the chemically amplifiable positive photoresist composition prepared as described above is applied to a support, and then the solvent is evaporated by heating, thereby forming a desired film. Examples of the method for applying the solution to the support include spin coating, slit coating, roll coating, screen printing, and applicator coating. The film of the composition of the present invention may be pre-baked usually at a temperature of from 70° C. to 150° C., preferably from 80° C. to 140° C. for about 2 to 60 minutes. The conditions vary depending on the types and blending ratio of the components in the composition, the thickness of the film, and the like.

The photoresist layer has a thickness of usually from 5 to 150 μm, preferably from 10 to 120 μm, more preferably from 10 to 100 μm.

To form a resist pattern using a resulting photoresist laminate, the photoresist layer is portion-selectively irradiated with (exposed to) light or radiation, such as ultraviolet light or visible light having a wavelength of from 300 to 500 nm through a prescribed pattern mask.

Herein, the term "light" refers to any light that can activate the photoacid generator to generate an acid and encompasses ultraviolet light, visible light, and far ultraviolet light. The term "radiation" refers to X-rays, electron beam, ion beam, or the like. Examples of the source of the light or radiation include low-pressure mercury lamps, high-pressure mercury lamps, ultra-high pressure mercury lamps, metal halide lamps, argon gas lasers, and LED lamps. For example, the dose of radiation exposure varies depending on the types and amounts of the components in the composition, the thickness of the film, and the like. For example, the dose using an ultra-high pressure mercury lamp is from 50 to 10,000 mJ/cm$^2$.

After exposure, the photoresist laminate is heated by a known method to promote acid diffusion, thereby changing the alkali solubility of the exposed part of the photoresist layer. Subsequently, unnecessary parts are dissolved and eliminated using a developer, for example, a prescribed alkali aqueous solution. Accordingly, a prescribed resist pattern is obtained.

The development time is usually 1 to 30 minutes. The time varies depending on the types and blending ratio of the components in the composition and the dry thickness of the composition film. The development may be performed by any technique, such as liquid filling, dipping, puddling, or spraying. After development, washing with running water is performed for 30 to 90 seconds, followed by drying using an air gun, an oven, or the like.

A conductor such as metal may be embedded to the resist-free parts (parts where the resist is removed by the alkaline developer) of the resist pattern by, for example, plating, whereby connecting terminals such as metal posts or bumps can be formed. Plating can be performed by any method, including conventionally known methods. Preferred examples of the plating liquid include solder plating, copper plating, gold plating, and nickel plating. Lastly, the remaining resist pattern is removed with a stripping solution by a conventional method.

The chemically amplifiable positive photoresist composition of the present invention can be used in the form of a dry film. The dry film includes a layer of the chemically amplifiable positive photoresist composition of the present invention and protective films formed on the respective faces of the layer. The layer of the chemically amplifiable positive photoresist composition has a thickness of usually from 10 to 150 μm, preferably from 20 to 120 μm, more preferably from 20 to 80 μm. Any protective film may be used, such as a resin film conventionally used for dry films. In an exemplary embodiment, a polyethylene terephthalate film is present on one face and a film selected from the group consisting of a polyethylene terephthalate film, a polypropylene film, and a polyethylene film is present on the other face.

For example, the chemically amplifiable positive dry film can be produced as follows: A solution of the chemically amplifiable positive photoresist composition prepared as described above is applied to one of the protective films, and then the solvent is evaporated by heating, thereby forming a desired film. Drying is performed usually at 60° C. to 100° C. for about 5 to 20 minutes. The drying conditions vary depending on the types and blending ratio of the components in the composition, the thickness of the film, and the like.

A resist pattern may be formed using the chemically amplifiable dry film as follows: One of the protective films on the chemically amplifiable positive dry film is peeled, and then the dry film is stacked on a support, with the peeled-side face facing the support, thereby preparing a photoresist layer. Next, the resist is dried by prebaking, and then the other protective film is peeled.

The thus obtained photoresist layer on the support can be processed into a resist pattern as described for the photoresist layer formed by direct application to a support.

The chemically amplifiable negative photoresist composition of the present invention contains: a component (E) containing the photoacid generator of the present invention that is a compound generating an acid when exposed to light or radiation; an alkali soluble resin (F) having a phenolic hydroxy group; and a crosslinking agent (G).

Alkali Soluble Resin (F) Having a Phenolic Hydroxy Group

Examples of the "alkali soluble resin having a phenolic hydroxy group" in the present invention (hereinafter, referred to as "phenolic resin (F)") include novolac resin, polyhydroxystyrene, polyhydroxystyrene copolymers, copolymers of hydroxystyrene and styrene, copolymers of hydroxystyrene, styrene, and a (meth)acrylic acid derivative, phenol-xylylene glycol condensation resin, cresol-xylylene glycol condensation resin, and phenol-dicyclopentadiene condensation resin. Preferred among these are novolac resin, polyhydroxystyrene, polyhydroxystyrene copolymers, copolymers of hydroxystyrene and styrene, copolymers of hydroxystyrene, styrene, and a (meth)acrylic acid derivative, and phenol-xylylene glycol condensation resin. The phenolic resin (F) may be used alone or in the admixture of two or more.

The phenolic resin (F) may contain a low molecular weight phenolic compound as one of the components thereof.

Examples of the low molecular weight phenolic compound include 4,4'-dihydroxydiphenyl methane and 4,4'-dihydroxydiphenyl ether.

Crosslinking Agent (G)

The "crosslinking agent" in the present invention (hereinafter, also referred to as "crosslinking agent (G)") may be any crosslinking agent functioning as a crosslinkable component (curing component) that reacts with the phenolic resin (F). Examples of the crosslinking agent (G) include compounds having at least two alkyl-etherified amino groups per molecule, compounds having at least two alkyl-etherified benzene skeletons per molecule, oxirane ring-containing compounds, thiirane ring-containing compounds, oxetanyl group-containing compounds, and isocyanate group-containing compounds (including blocks thereof).

Of these, the crosslinking agent (G) is preferably a compound having at least two alkyl-etherified amino groups per molecule or an oxirane ring-containing compound. It is more preferably a combination of a compound having at least two alkyl-etherified amino groups per molecule and an oxirane ring-containing compound.

The amount of the crosslinking agent (G) in the present invention per 100 parts by weight of the phenolic resin (F) is preferably from 1 to 100 parts by weight, more preferably from 5 to 50 parts by weight. When the amount of the crosslinking agent (G) is from 1 to 100 parts by weight, preferably, a curing reaction can sufficiently proceed, and a resulting cured product has high resolution, good pattern shape, excellent heat resistance, and excellent electrical insulation.

When a compound having alkyl-etherified amino groups and an oxirane ring-containing compound are used in combination, the oxirane ring-containing compound content in total 100% by weight of the compound having alkyl-etherified amino groups and the oxirane ring-containing compound is preferably 50% by weight or lower, more preferably 5 to 40% by weight, particularly preferably 5 to 30% by weight.

The above content is preferred because the resulting cured film can have excellent chemical resistance without losing high resolution properties.

Crosslinked Fine Particles (H)

The chemically amplifiable negative photoresist composition of the present invention may further contain crosslinked fine particles (hereinafter, also referred to as "crosslinked fine particles (H)") to enhance the durability or heat impact resistance of resulting cured products.

The crosslinked fine particles (H) have an average particle size of usually 30 to 500 nm, preferably 40 to 200 nm, still more preferably 50 to 120 nm.

The particle size of the crosslinked fine particles (H) may be controlled by any method. For example, when the crosslinked fine particles are synthesized by emulsion polymerization, the particle size can be controlled by changing the amount of an emulsifier to control the number of micelles during the emulsion polymerization.

The average particle size of the crosslinked fine particles (H) is a value measured with a light scattering flow distribution measuring device or the like using a dispersion of the crosslinked fine particles diluted by a usual method.

The amount of the crosslinked fine particles (H) per 100 parts by weight of the phenolic resin (F) is preferably from 0.5 to 50 parts by weight, more preferably from 1 to 30 parts by weight. When the amount of the crosslinked fine particles (H) is from 0.5 to 50 parts by weight, excellent compatibility with other components or excellent dispersion is obtained, and the heat impact resistance and heat resistance of a resulting cured film can be improved.

Adhesion Aid

The chemically amplifiable negative photoresist composition of the present invention may contain an adhesion aid to enhance adhesion to a substrate.

Examples of the adhesion aid include functional silane coupling agents having reactive substituents such as carboxyl groups, methacryloyl groups, isocyanate groups, and epoxy groups.

The amount of the adhesion aid per 100 parts by weight of the phenolic resin (F) is preferably from 0.2 to 10 parts by weight, more preferably from 0.5 to 8 parts by weight. When the amount of the adhesion aid is from 0.2 to 10 parts by weight, preferably, not only excellent storage stability but also good adhesion can be obtained.

Solvent

The chemically amplifiable negative photoresist composition of the present invention may contain a solvent to improve the handleability of the resin composition or to control the viscosity or storage stability.

Any solvent may be used, and specific examples thereof include those mentioned above.

The chemically amplifiable negative photoresist composition of the present invention may contain a sensitizer, if necessary. Examples of the sensitizer include conventionally known ones, and specific examples thereof include those mentioned above.

The amount of the sensitizer relative to total 100 parts by weight of the sulfonium salt represented by the formula (1) is from 5 to 500 parts by weight, preferably from 10 to 300 parts by weight.

The chemically amplifiable negative photoresist composition of the present invention may contain other additives, if necessary, as long as the features of the present invention are not impaired. Examples of other additives include inorganic filler, quenchers, leveling agents, and surfactants.

The chemically amplifiable negative photoresist composition of the present invention may be prepared by any method including known methods. It may be prepared by stirring a completely sealed sample vessel containing the components on a wave rotor.

The cured product of the present invention is obtainable by curing the chemically amplifiable negative photoresist composition.

The chemically amplifiable negative photoresist composition of the present invention has a high film-remaining ratio and excellent resolution properties. A cured product thereof has excellent electrical insulation, excellent heat impact resistance, and the like. Thus, the cured product is preferably used as a surface protective film, a planarizing film, an interlayer insulating film material, or the like of electronic components such as semiconductor devices and semiconductor packages.

The cured product of the present invention is produced as follows: First, the chemically amplifiable negative photoresist composition of the present invention is applied to a support (e.g., resin-coated copper foil, copper clad laminate, or silicon wafer or alumina substrate having a sputtered metal film) and then dried to evaporate a solvent, thereby forming a film. Then, the film is exposed to light through a desired pattern mask. Subsequently, the film is heated (hereinafter, this heat treatment is referred to as "PEB") to promote the reaction between the phenolic resin (F) and the crosslinking agent (G). Next, development is performed using an alkaline developer, and unexposed parts are dissolved and removed, thereby forming a desired pattern. Thereafter, heat treatment is performed for the expression of insulating film properties. Accordingly, a cured product is obtained.

Examples of the method to apply the resin composition to the support include dipping, spraying, bar coating, roll coating, and spin coating. The film thickness may be appropriately controlled by changing the application technique or changing the solid concentration or viscosity of composition solutions.

Examples of the radiation for the exposure include ultraviolet light, electron beam, and laser beam irradiated by low-pressure mercury lamps, high-pressure mercury lamps, metal halide lamps, g-ray steppers, h-ray steppers, i-ray steppers, gh-ray steppers, and ghi-ray steppers. The exposure dose is appropriately selected depending on the light source to be used, the resin film thickness, or the like. For example, when the exposure is performed by irradiating ultraviolet light from a high-pressure mercury lamp, the dose for a resin film having a thickness of 1 to 50 μm is about 100 to 50,000 J/m².

After exposure, the PEB treatment is performed to promote the curing reaction by the action of a generated acid between the phenolic resin (F) and the crosslinking agent (G). The PEB conditions vary depending on the amount of the resin composition, film thickness, or the like. The PEB treatment is performed usually at 70° C. to 150° C., preferably 80° C. to 120° C. for about one to 60 minutes. Next, development is performed using an alkaline developer, and unexposed parts are dissolved and removed, thereby forming a desired pattern. Examples of the method of development include shower development, spray development, immersion development, and puddle development. The development is performed usually at 20° C. to 40° C. for about one to 10 minutes.

The film after development is sufficiently cured by heating to fully expressing the properties as an insulating film. The curing conditions are not limited and are set depending on the intended use of a cured product. The composition may be cured by heating at a temperature of 50° C. to 250° C. for about 30 minutes to 10 hours. The heating may include two stages for sufficient curing or prevention of the deformation of resulting pattern shapes. For example, the composition may be cured by heating at a temperature of 50° C. to 120° C. for about five minutes to two hours at the first stage, and then at a temperature of 80° C. to 250° C. for about 10 minutes to 10 hours. A heating device such as a usual oven or an infrared heating furnace may be used under the above-mentioned curing conditions.

EXAMPLES

The present invention will be specifically described with reference to examples and comparative examples, but the present invention is not limited thereto. The term "part(s)" in those examples mean "part(s) by weight".

(Example 1) Synthesis of [2-methyl-4-(2-thioxanthonylthio)phenyl](3-methylphenyl) (2-thioxanthonyl)sulfonium Methane Sulfonate (P1-MS)

[Chem. 8]

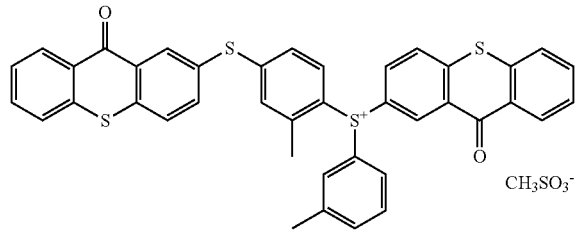

(P1-MS)

CH$_3$SO$_3^-$

An amount of 1.0 part of 2-[(3-methylphenyl)sulfinyl]thioxanthone, 1.0 part of 2-[(3-methylphenyl)thio]thioxanthone, 5.9 parts of acetic anhydride, and 2.3 parts of methanesulfonic acid were homogeneously mixed and reacted at 65° C. for six hours. The reaction solution was cooled to room temperature, poured into 10 parts of ion exchange water, and extracted with 10 parts of dichloromethane. The aqueous phase was removed, and 10 parts of ion exchange water was again fed to wash the organic phase. The organic phase-washing operation was repeated until the pH of the aqueous phase became neutral. Next, unreacted raw materials were eliminated by repeating three times a series of operations involving addition of 15 parts of cyclohexane to the organic phase, stirring, leaving at rest for 30 minutes, and removal of an upper phase. Next, the lower phase was transferred to a rotary evaporator, and the solvent was evaporated. Accordingly, 1.5 parts of a compound (P1-MS) was obtained. The product was identified by $^1$H-NMR and LC-MS.

(Example 2) Synthesis of [2-methyl-4-(2-thioxanthonylthio)phenyl](3-methylphenyl) (2-thioxanthonyl)sulfonium Trifluoromethane Sulfonate (P1-TF)

[Chem. 9]

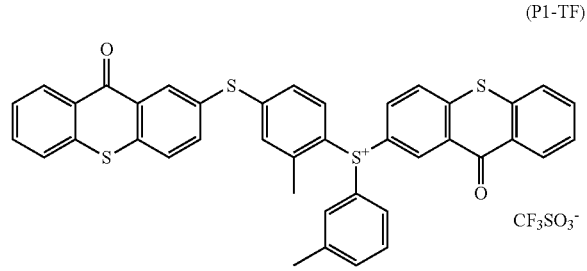

(P1-TF)

CF$_3$SO$_3^-$

The [2-methyl-4-(2-thioxanthonylthio)phenyl](3-methylphenyl) (2-thioxanthonyl)sulfonium methane sulfonate (P1-MS) synthesized in Example 1 in an amount of 1.0 part was dissolved in 6.7 parts of dichloromethane. To the solution were added 0.3 parts of potassium trifluoromethane sulfonate and 5.9 parts of ion exchange water, followed by stirring at room temperature for one hour. Subsequently, the organic phase was washed with 6 parts of ion exchange water five times. Next, the organic phase was transferred to a rotary evaporator, and the solvent was evaporated. Accordingly, 0.96 parts of P1-TF was obtained. The product was identified by $^1$H-NMR and $^{19}$F-NMR.

(Example 3) Synthesis of [2-methyl-4-(2-thioxanthonylthio)phenyl](3-methylphenyl) (2-thioxanthonyl)sulfonium Nonafluorobutane Sulfonate (P1-NF)

[Chem. 10]

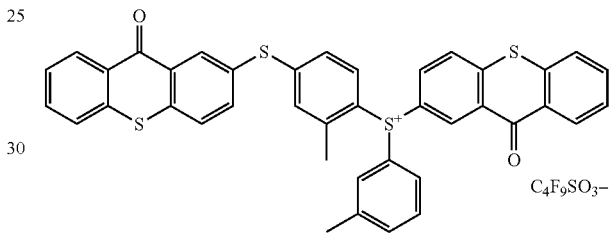

(P1-NF)

C$_4$F$_9$SO$_3-$

P1-NF in an amount of 1.1 parts was obtained as in Example 2, except that "0.3 parts of potassium trifluoromethane sulfonate" in Example 2 was changed to "0.47 parts of potassium nonafluorobutane sulfonate". The product was identified by $^1$H-NMR and $^{19}$F-NMR.

(Example 4) Synthesis of [2-methyl-4-(2-thioxanthonylthio)phenyl](3-methylphenyl) (2-thioxanthonyl)sulfonium Hexafluorophosphate (P1-P)

[Chem. 11]

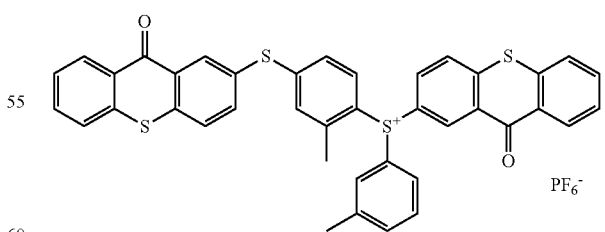

(P1-P)

PF$_6^-$

P1-P in an amount of 0.96 parts was obtained as in Example 2, except that "0.3 parts of potassium trifluoromethane sulfonate" in Example 2 was changed to "0.3 parts of potassium hexafluorophosphate". The product was identified by $^1$H-NMR and $^{19}$F-NMR.

(Example 5) Synthesis of [2-methyl-4-(2-thioxanthonylthio)phenyl](3-methylphenyl) (2-thioxanthonyl)sulfonium tetrakis(pentafluorophenyl) Borate (P1-B)

[Chem. 12]

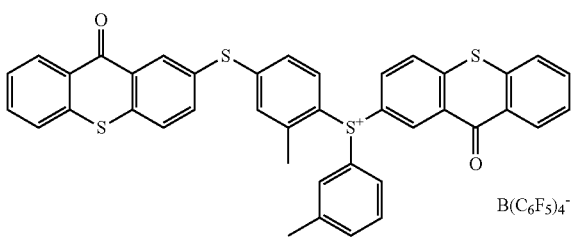

(P1-B)

B(C₆F₅)₄⁻

P1-B in an amount of 1.6 parts was obtained as in Example 2, except that "0.3 parts of potassium trifluoromethane sulfonate" in Example 2 was changed to "0.97 parts of sodium tetrakis(pentafluorophenyl) borate". The product was identified by $^1$H-NMR and $^{19}$F-NMR.

(Example 6) Synthesis of [2-methyl-4-(2-thioxanthonylthio)phenyl](3-methylphenyl) (2-thioxanthonyl)sulfonium tris(pentafluoroethyl) Trifluorophosphate (P1-FP)

[Chem. 13]

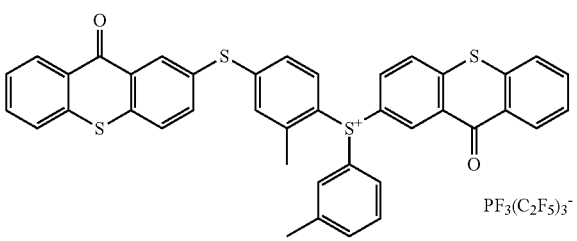

(P1-FP)

PF₃(C₂F₅)₃⁻

P1-FP in an amount of 1.3 parts was obtained as in Example 2, except that "0.3 parts of potassium trifluoromethane sulfonate" in Example 2 was changed to "0.67 parts of potassium tris(pentafluoroethyl) trifluorophosphate". The product was identified by $^1$H-NMR and $^{19}$F-NMR.

(Example 7) Synthesis of [2-methyl-4-(2-thioxanthonylthio)phenyl](3-methylphenyl) (2-thioxanthonyl)sulfonium Hexafluoroantimonate (P1-SB)

[Chem. 14]

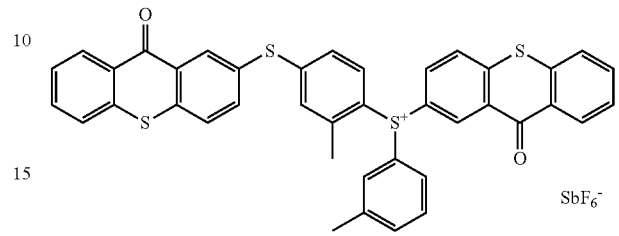

(P1-SB)

SbF₆⁻

P1-SB in an amount of 1.0 part was obtained as in Example 2, except that "0.3 parts of potassium trifluoromethane sulfonate" in Example 2 was changed to "0.73 parts of potassium hexafluoroantimonate". The product was identified by $^1$H-NMR and $^{19}$F-NMR.

(Example 8) Synthesis of [2-methyl-4-(2-thioxanthonylthio)phenyl](3-methylphenyl) (2-thioxanthonyl)sulfonium tetrakis(pentafluorophenyl) Gallate (P1-GA)

[Chem. 15]

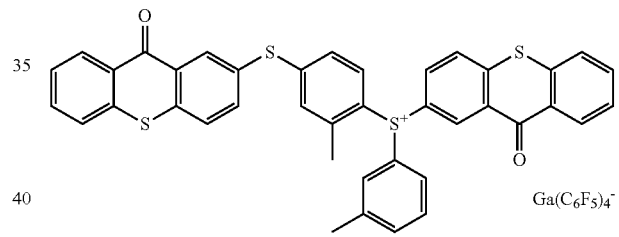

(P1-GA)

Ga(C₆F₅)₄⁻

P1-GA in an amount of 1.6 parts was obtained as in Example 2, except that "0.3 parts of potassium trifluoromethane sulfonate" in Example 2 was changed to "1.06 parts of sodium tetrakis(pentafluorophenyl) gallate". The product was identified by $^1$H-NMR and $^{19}$F-NMR.

(Example 9) Synthesis of [2-methoxy-4-(2-thioxanthonylthio)phenyl](3-methoxyphenyl) (2-thioxanthonyl)sulfonium Methane Sulfonate (P2-MS)

[Chem. 16]

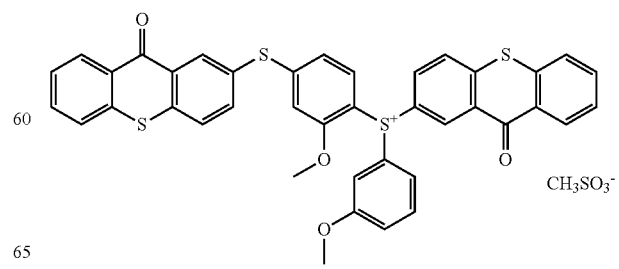

(P2-MS)

CH₃SO₃⁻

An amount of 1.0 part of 2-[(3-methoxyphenyl)sulfinyl]thioxanthone, 1.0 part of 2-[(3-methoxyphenyl)thio]thioxanthone, 5.6 parts of acetic anhydride, and 2.1 parts of methanesulfonic acid were homogeneously mixed and reacted at 65° C. for six hours. The reaction solution was cooled to room temperature, poured into 10 parts of ion exchange water, and extracted with 10 parts of dichloromethane. The aqueous phase was removed, and 10 parts of ion exchange water was again fed to wash the organic phase. The organic phase-washing operation was repeated until the pH of the aqueous phase became neutral. Next, unreacted raw materials were eliminated by repeating three times a series of operations involving addition of 15 parts of cyclohexane to the organic phase, stirring, leaving at rest for 30 minutes, and removal of an upper phase. Next, the lower phase was transferred to a rotary evaporator, and the solvent was evaporated. Accordingly, 1.5 parts of a compound (P2-MS) was obtained. The product was identified by $^1$H-NMR and LC-MS.

(Example 10) Synthesis of [2-methoxy-4-(2-thioxanthonylthio)phenyl](3-methoxyphenyl) (2-thioxanthonyl)sulfonium Trifluoromethane Sulfonate (P2-TF)

[Chem. 17]

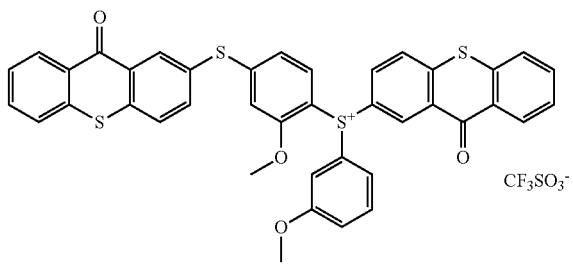

(P2-TF)

The [2-methoxy-4-(2-thioxanthonylthio)phenyl](3-methoxyphenyl) (2-thioxanthonyl)sulfonium methane sulfonate (P2-MS) synthesized in Example 9 in an amount of 1.0 part was dissolved in 6.4 parts of dichloromethane. To the solution were added 0.25 parts of potassium trifluoromethane sulfonate and 5.7 parts of ion exchange water, followed by stirring at room temperature for one hour. Subsequently, the organic phase was washed with 6 parts of ion exchange water five times. Next, the organic phase was transferred to a rotary evaporator, and the solvent was evaporated. Accordingly, 0.96 parts of P2-TF was obtained. The product was identified by $^1$H-NMR and $^{19}$F-NMR.

(Example 11) Synthesis of [2-methoxy-4-(2-thioxanthonylthio)phenyl](3-methoxyphenyl) (2-thioxanthonyl)sulfonium Nonafluorobutane Sulfonate (P2-NF)

[Chem. 18]

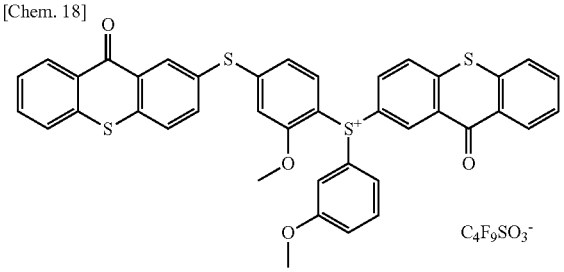

(P2-NF)

P2-NF in an amount of 1.1 parts was obtained as in Example 10, except that "0.25 parts of potassium trifluoromethane sulfonate" in Example 10 was changed to "0.45 parts of potassium nonafluorobutane sulfonate". The product was identified by $^1$H-NMR and $^{19}$F-NMR.

(Example 12) Synthesis of [2-methoxy-4-(2-thioxanthonylthio)phenyl](3-methoxyphenyl) (2-thioxanthonyl)sulfonium Hexafluorophosphate (P2-P)

[Chem. 19]

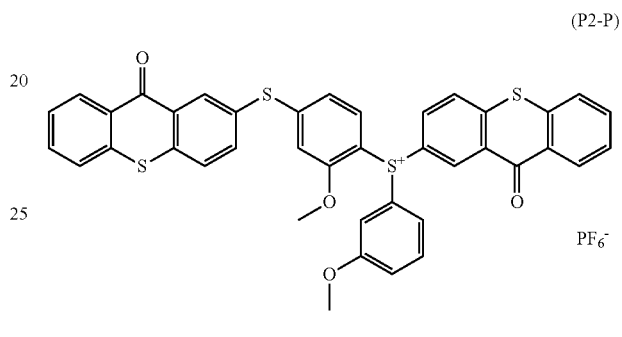

(P2-P)

P2-P in an amount of 1.0 part was obtained as in Example 10, except that "0.25 parts of potassium trifluoromethane sulfonate" in Example 10 was changed to "0.25 parts of potassium hexafluorophosphate". The product was identified by $^1$H-NMR and $^{19}$F-NMR.

(Example 13) Synthesis of [2-methoxy-4-(2-thioxanthonylthio)phenyl](3-methoxyphenyl) (2-thioxanthonyl)sulfonium tetrakis(pentafluorophenyl) Borate (P2-B)

[Chem. 20]

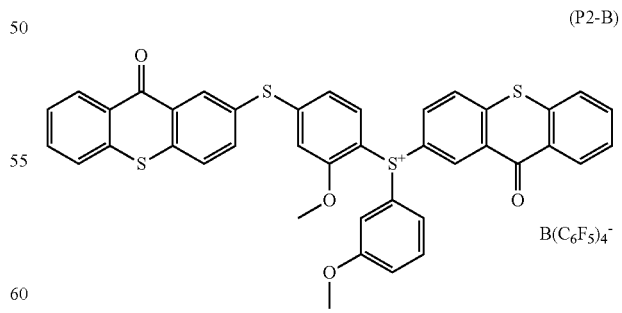

(P2-B)

P2-B in an amount of 1.5 parts was obtained as in Example 10, except that "0.25 parts of potassium trifluoromethane sulfonate" in Example 10 was changed to "0.93 parts of sodium tetrakis(pentafluorophenyl) borate". The product was identified by $^1$H-NMR and $^{19}$F-NMR.

(Example 14) Synthesis of [2-methoxy-4-(2-thio-xanthonylthio)phenyl](3-methoxyphenyl) (2-thio-xanthonyl)sulfonium tris(pentafluoroethyl) Trifluorophosphate (P2-FP)

[Chem. 21]

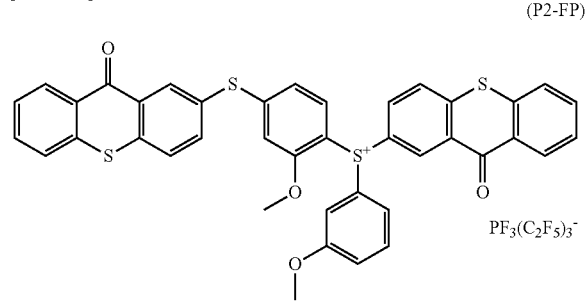

(P2-FP)

PF$_3$(C$_2$F$_5$)$_3^-$

P2-FP in an amount of 1.3 parts was obtained as in Example 10, except that "0.25 parts of potassium trifluoromethane sulfonate" in Example 10 was changed to "0.64 parts of potassium tris(pentafluoroethyl) trifluorophosphate". The product was identified by $^1$H-NMR and $^{19}$F-NMR.

(Example 15) Synthesis of [2-methoxy-4-(2-thio-xanthonylthio)phenyl](3-methoxyphenyl) (2-thio-xanthonyl)sulfonium Hexafluoroantimonate (P2-SB)

[Chem. 22]

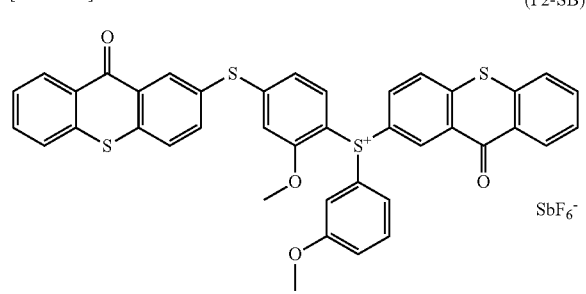

(P2-SB)

SbF$_6^-$

P2-SB in an amount of 1.0 part was obtained as in Example 10, except that "0.25 parts of potassium trifluoromethane sulfonate" in Example 10 was changed to "0.70 parts of potassium hexafluoroantimonate". The product was identified by $^1$H-NMR and $^{19}$F-NMR.

(Example 16) Synthesis of [2-methoxy-4-(2-thio-xanthonylthio)phenyl](3-methoxyphenyl) (2-thio-xanthonyl)sulfonium tetrakis(pentafluorophenyl) Gallate (P2-GA)

[Chem. 23]

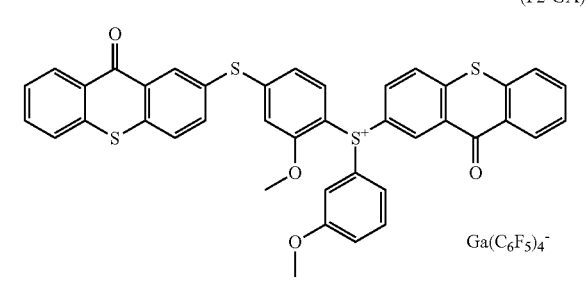

(P2-GA)

Ga(C$_6$F$_5$)$_4^-$

P2-GA in an amount of 1.6 parts was obtained as in Example 10, except that "0.25 parts of potassium trifluoromethane sulfonate" in Example 10 was changed to "1.01 parts of sodium tetrakis(pentafluorophenyl) gallate". The product was identified by $^1$H-NMR and $^{19}$F-NMR.

(Example 17) Synthesis of [2-tert-butyl-4-(2-thio-xanthonylthio)phenyl](3-tert-butylphenyl) (2-thio-xanthonyl)sulfonium Methane Sulfonate (P3-MS)

[Chem. 24]

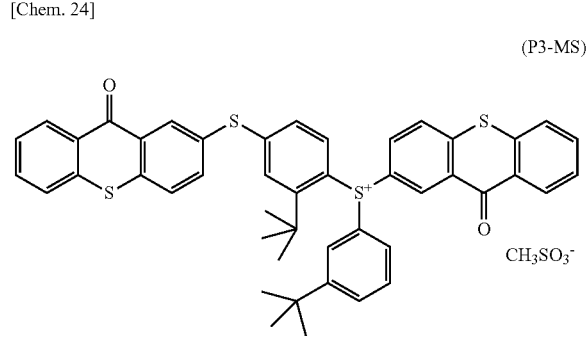

(P3-MS)

CH$_3$SO$_3^-$

An amount of 1.0 part of 2-[(3-tert-butylphenyl)sulfinyl]thioxanthone, 1.0 part of 2-[(3-tert-butylphenyl)thio]thioxanthone, 5.0 parts of acetic anhydride, and 1.9 parts of methanesulfonic acid were homogeneously mixed and reacted at 65° C. for six hours. The reaction solution was cooled to room temperature, poured into 10 parts of ion exchange water, and extracted with 10 parts of dichloromethane. The aqueous phase was removed, and 10 parts of ion exchange water was again fed to wash the organic phase. The organic phase-washing operation was repeated until the pH of the aqueous phase became neutral.

Next, unreacted raw materials were eliminated by repeating three times a series of operations involving addition of 15 parts of cyclohexane to the organic phase, stirring, leaving at rest for 30 minutes, and removal of an upper phase. Next, the lower phase was transferred to a rotary evaporator, and the solvent was evaporated. Accordingly, 1.5 parts of a compound (P3-MS) was obtained. The product was identified by $^1$H-NMR and LC-MS.

(Example 18) Synthesis of [2-tert-butyl-4-(2-thio-xanthonylthio)phenyl](3-tert-butylphenyl) (2-thio-xanthonyl)sulfonium Trifluoromethane Sulfonate (P3-TF)

[Chem. 25]

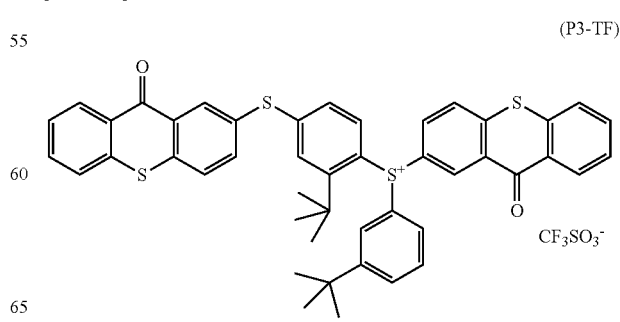

(P3-TF)

CF$_3$SO$_3^-$

The [2-tert-butyl-4-(2-thioxanthonylthio)phenyl](3-tert-butylphenyl) (2-thioxanthonyl)sulfonium methane sulfonate (P3-MS) synthesized in Example 17 in an amount of 1.0 part was dissolved in 5.8 parts of dichloromethane. To the solution were added 0.23 parts of potassium trifluoromethane sulfonate and 5.1 parts of ion exchange water, followed by stirring at room temperature for one hour. Subsequently, the organic phase was washed with 5 parts of ion exchange water five times. Next, the organic phase was transferred to a rotary evaporator, and the solvent was evaporated. Accordingly, 0.96 parts of P3-TF was obtained. The product was identified by $^1$H-NMR and $^{19}$F-NMR.

(Example 19) Synthesis of [2-tert-butyl-4-(2-thioxanthonylthio)phenyl](3-tert-butylphenyl) (2-thioxanthonyl)sulfonium Trifluorobutane Sulfonate (P3-NF)

[Chem. 26]

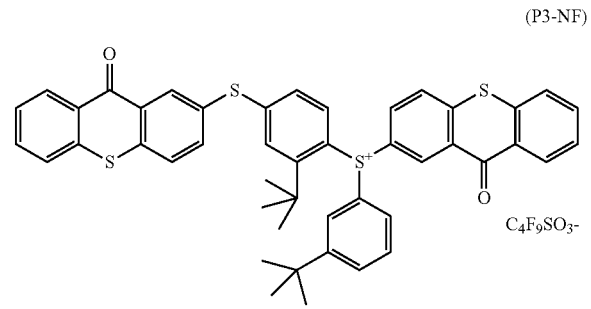

(P3-NF)

C$_4$F$_9$SO$_3$-

P3-NF in an amount of 1.1 parts was obtained as in Example 18, except that "0.23 parts of potassium trifluoromethane sulfonate" in Example 18 was changed to "0.41 parts of potassium nonafluorobutane sulfonate". The product was identified by $^1$H-NMR and $^{19}$F-NMR.

(Example 20) Synthesis of [2-tert-butyl-4-(2-thioxanthonylthio)phenyl](3-tert-butylphenyl) (2-thioxanthonyl)sulfonium Hexafluorophosphate (P3-P)

[Chem. 27]

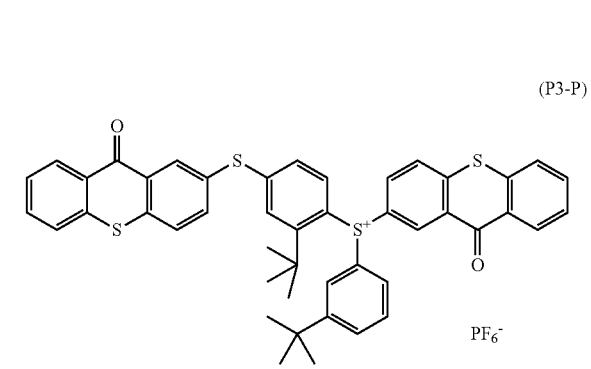

(P3-P)

PF$_6$-

P3-NF in an amount of 0.95 parts was obtained as in Example 18, except that "0.23 parts of potassium trifluoromethane sulfonate" in Example 18 was changed to "0.22 parts of potassium hexafluorophosphate". The product was identified by $^1$H-NMR and $^{19}$F-NMR.

(Example 21) Synthesis of [2-tert-butyl-4-(2-thioxanthonylthio)phenyl](3-tert-butylphenyl) (2-thioxanthonyl)sulfonium tetrakis(pentafluorophenyl) Borate (P3-B)

[Chem. 28]

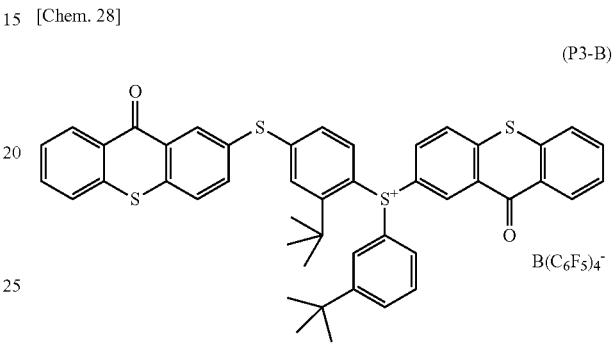

(P3-B)

B(C$_6$F$_5$)$_4$-

P3-B in an amount of 1.5 parts was obtained as in Example 18, except that "0.23 parts of potassium trifluoromethane sulfonate" in Example 18 was changed to "0.85 parts of sodium tetrakis(pentafluorophenyl) borate". The product was identified by $^1$H-NMR and $^{19}$F-NMR.

(Example 22) Synthesis of [2-tert-butyl-4-(2-thioxanthonylthio)phenyl](3-tert-butylphenyl) (2-thioxanthonyl)sulfonium tris(pentafluoroethyl) Trifluorophosphate (P3-FP)

[Chem. 29]

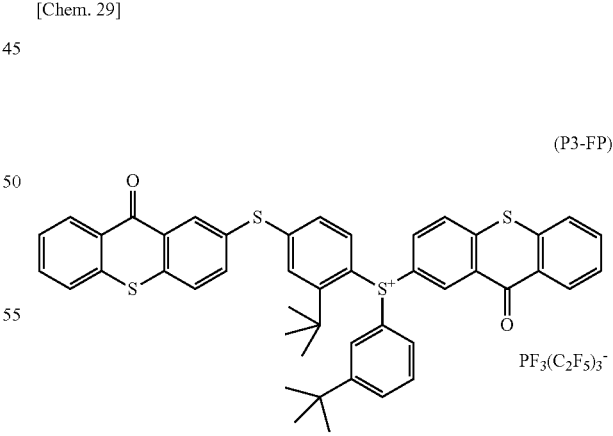

(P3-FP)

PF$_3$(C$_2$F$_5$)$_3$-

P3-FP in an amount of 1.26 parts was obtained as in Example 18, except that "0.23 parts of potassium trifluoromethane sulfonate" in Example 18 was changed to "0.59 parts of potassium tris(pentafluoroethyl) trifluorophosphate". The product was identified by $^1$H-NMR and $^{19}$F-NMR.

(Example 23) Synthesis of [2-tert-butyl-4-(2-thioxanthonylthio)phenyl](3-tert-butylphenyl) (2-thioxanthonyl)sulfonium Hexafluoroantimonate (P3-SB)

[Chem. 30]

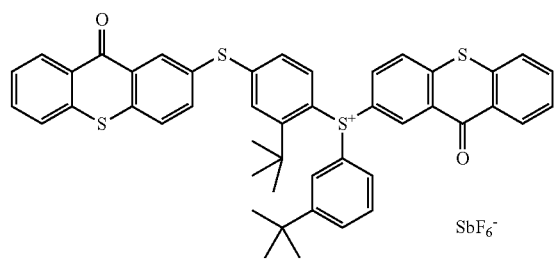

(P3-SB)

P3-SB in an amount of 1.05 parts was obtained as in Example 18, except that "0.23 parts of potassium trifluoromethane sulfonate" in Example 18 was changed to "0.63 parts of potassium hexafluoroantimonate". The product was identified by $^1$H-NMR and $^{19}$F-NMR.

(Example 24) Synthesis of [2-tert-butyl-4-(2-thioxanthonylthio)phenyl](3-tert-butylphenyl) (2-thioxanthonyl)sulfonium tetrakis(pentafluorophenyl) Gallate (P3-GA)

[Chem. 31]

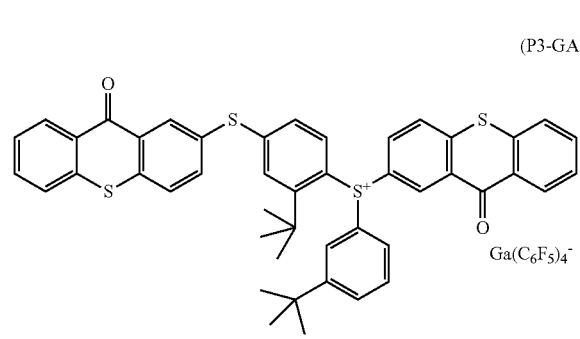

(P3-GA)

P3-GA in an amount of 1.56 parts was obtained as in Example 18, except that "0.23 parts of potassium trifluoromethane sulfonate" in Example 18 was changed to "0.92 parts of sodium tetrakis(pentafluorophenyl) gallate". The product was identified by $^1$H-NMR and $^{19}$F-NMR.

(Example 25) Synthesis of [2,6-dimethyl-4-(2-thioxanthonylthio)phenyl](3,5-dimethylphenyl) (2-thioxanthonyl)sulfonium Methane Sulfonate (P4-MS)

[Chem. 32]

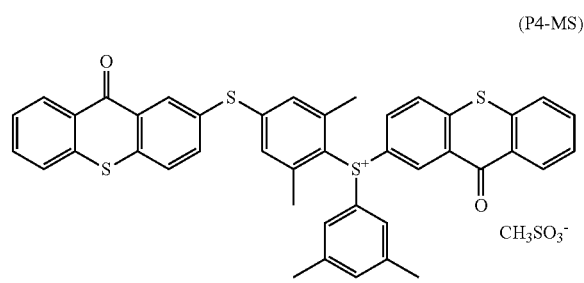

(P4-MS)

P4-MS in an amount of 1.5 parts was obtained as in Example 9, except that "1.0 part of 2-[(3-methoxyphenyl)sulfinyl]thioxanthone and 1.0 part of 2-[(3-methoxyphenyl)thio]thioxanthone" in Example 9 were changed to "1.0 part of 2-[(3,5-dimethylphenyl)sulfinyl]thioxanthone and 1.0 part of 2-[(3,5-dimethylphenyl)thio]thioxanthone". The product was identified by $^1$H-NMR and LC-MS.

(Example 26) Synthesis of [2,6-dimethyl-4-(2-thioxanthonylthio)phenyl](3,5-dimethylphenyl) (2-thioxanthonyl)sulfonium Trifluoromethane Sulfonate (P4-TF)

[Chem. 33]

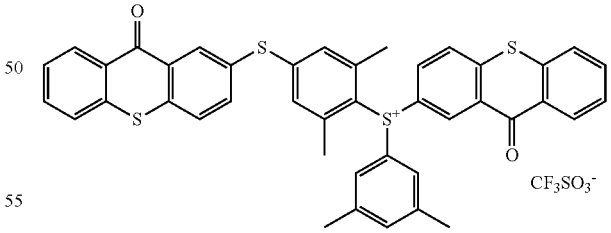

(P4-TF)

P4-TF in an amount of 1.0 part was obtained as in Example 10, except that "1.0 part of the [2-methoxy-4-(2-thioxanthonylthio)phenyl](3-methoxyphenyl) (2-thioxanthonyl)sulfonium methane sulfonate (P2-MS) synthesized in Example 9" in Example 10 was changed to "1.0 part of the [2,6-dimethyl-4-(2-thioxanthonylthio)phenyl](3,5-dimethylphenyl) (2-thioxanthonyl)sulfonium methane sulfonate (P4-MS) synthesized in Example 25". The product was identified by $^1$H-NMR and $^{19}$F-NMR.

(Example 27) Synthesis of [2,6-dimethyl-4-(2-thioxanthonylthio)phenyl](3,5-dimethylphenyl) (2-thioxanthonyl)sulfonium Nonafluorobutane Sulfonate (P4-NF)

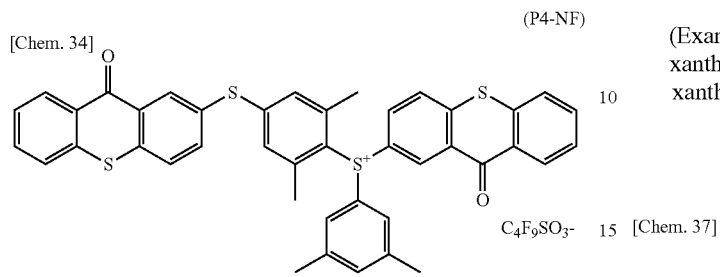

(P4-NF)

C$_4$F$_9$SO$_3^-$

P4-NF in an amount of 1.1 parts was obtained as in Example 26, except that "0.25 parts of potassium trifluoromethane sulfonate" in Example 26 was changed to "0.45 parts of potassium trifluorobutane sulfonate". The product was identified by $^1$H-NMR and $^{19}$F-NMR.

(Example 28) Synthesis of [2,6-dimethyl-4-(2-thioxanthonylthio)phenyl](3,5-dimethylphenyl) (2-thioxanthonyl)sulfonium Hexafluorophosphate (P4-P)

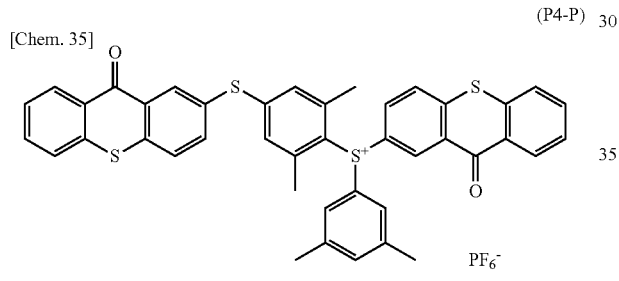

(P4-P)

PF$_6^-$

P4-P in an amount of 0.96 parts was obtained as in Example 26, except that "0.25 parts of potassium trifluoromethane sulfonate" in Example 26 was changed to "0.25 parts of potassium hexafluorophosphate". The product was identified by $^1$H-NMR and $^{19}$F-NMR.

(Example 29) Synthesis of [2,6-dimethyl-4-(2-thioxanthonylthio)phenyl](3,5-dimethylphenyl) (2-thioxanthonyl)sulfonium tetrakis(pentafluorophenyl) Borate (P4-B)

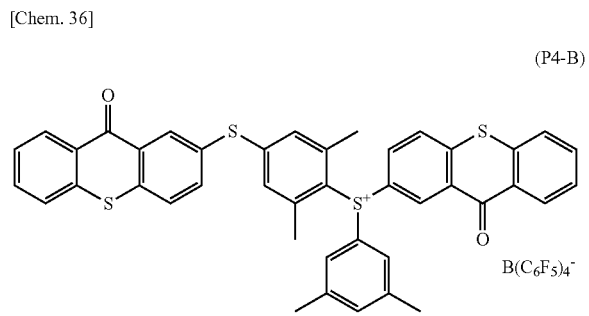

(P4-B)

B(C$_6$F$_5$)$_4^-$

P4-B in an amount of 1.56 parts was obtained as in Example 26, except that "0.25 parts of potassium trifluoromethane sulfonate" in Example 26 was changed to "0.94 parts of sodium tetrakis(pentafluorophenyl) borate". The product was identified by $^1$H-NMR and $^{19}$F-NMR.

(Example 30) Synthesis of [2,6-dimethyl-4-(2-thioxanthonylthio)phenyl](3,5-dimethylphenyl) (2-thioxanthonyl)sulfonium tris(pentafluoroethyl) Trifluorophosphate (P4-FP)

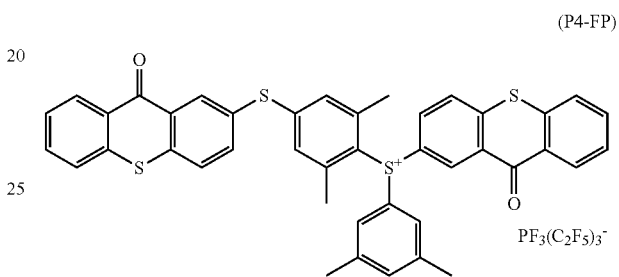

(P4-FP)

PF$_3$(C$_2$F$_5$)$_3^-$

P4-FP in an amount of 1.30 parts was obtained as in Example 26, except that "0.25 parts of potassium trifluoromethane sulfonate" in Example 26 was changed to "0.65 parts of potassium tris(pentafluoroethyl) trifluorophosphate". The product was identified by $^1$H-NMR and $^{19}$F-NMR.

(Example 31) Synthesis of [2,6-dimethyl-4-(2-thioxanthonylthio)phenyl](3,5-dimethylphenyl) (2-thioxanthonyl)sulfonium Hexafluoroantimonate (P4-SB)

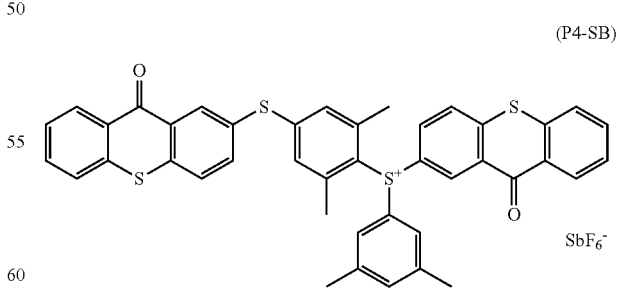

(P4-SB)

SbF$_6^-$

P4-SB in an amount of 1.06 parts was obtained as in Example 26, except that "0.25 parts of potassium trifluoromethane sulfonate" in Example 26 was changed to "0.70 parts of potassium hexafluoroantimonate". The product was identified by $^1$H-NMR and $^{19}$F-NMR.

(Example 32) Synthesis of [2,6-dimethyl-4-(2-thioxanthonylthio)phenyl](3,5-dimethylphenyl) (2-thioxanthonyl)sulfonium tetrakis(pentafluorophenyl) Gallate (P4-GA)

[Chem. 39]

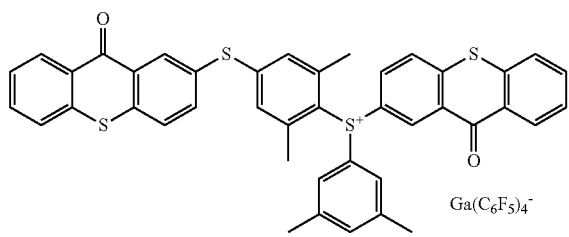

(P4-GA)

P4-GA in an amount of 1.63 parts was obtained as in Example 26, except that "0.25 parts of potassium trifluoromethane sulfonate" in Example 26 was changed to "1.02 parts of tetrakis(pentafluorophenyl) gallate". The product was identified by $^1$H-NMR and $^{19}$F-NMR.

(Example 33) Synthesis of [2,5-dimethyl-4-(2-thioxanthonylthio)phenyl](2,5-dimethylphenyl) (2-thioxanthonyl)sulfonium Methane Sulfonate (P5-MS)

[Chem. 40]

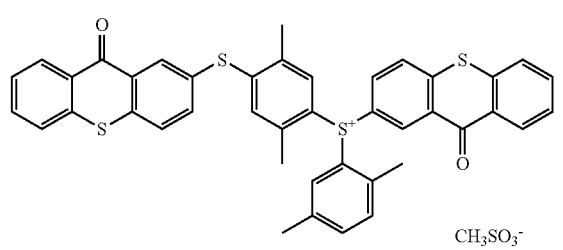

(P5-MS)

P5-MS in an amount of 1.5 parts was obtained as in Example 9, except that "1.0 part of 2-[(3-methoxyphenyl)sulfinyl]thioxanthone and 1.0 part of 2-[(3-methoxyphenyl)thio]thioxanthone" in Example 9 were changed to "1.0 part of 2-[(2,5-dimethylphenyl)sulfinyl]thioxanthone and 1.0 part of 2-[(2,5-dimethylphenyl)thio]thioxanthone". The product was identified by $^1$H-NMR and LC-MS.

(Example 34) Synthesis of [2,5-dimethyl-4-(2-thioxanthonylthio)phenyl](2,5-dimethylphenyl) (2-thioxanthonyl)sulfonium Trifluoromethane Sulfonate (P5-TF)

[Chem. 41]

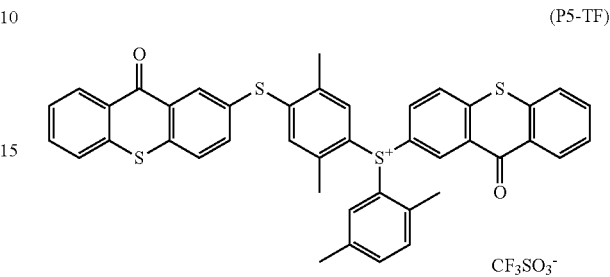

(P5-TF)

P5-TF in an amount of 0.96 parts was obtained as in Example 10, except that "1.0 part of the [2-methoxy-4-(2-thioxanthonylthio)phenyl](3-methoxyphenyl) (2-thioxanthonyl)sulfonium methane sulfonate (P2-MS) synthesized in Example 9" in Example 10 was changed to "1.0 part of the [2,5-dimethyl-4-(2-thioxanthonylthio)phenyl](2,5-dimethylphenyl) (2-thioxanthonyl)sulfonium methane sulfonate (P5-MS) synthesized in Example 33". The product was identified by $^1$H-NMR and $^{19}$F-NMR.

(Example 35) Synthesis of [2,5-dimethyl-4-(2-thioxanthonylthio)phenyl](2,5-dimethylphenyl) (2-thioxanthonyl)sulfonium Nonafluorobutane Sulfonate (P5-NF)

[Chem. 42]

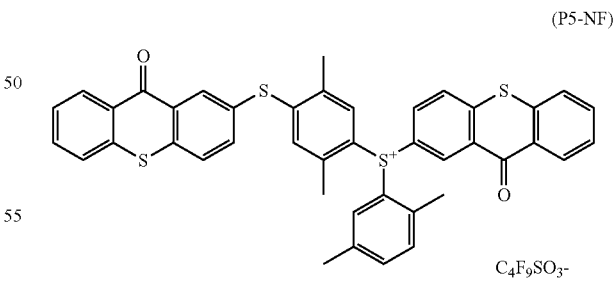

(P5-NF)

P5-NF in an amount of 1.13 parts was obtained as in Example 34, except that "0.25 parts of potassium trifluoromethane sulfonate" in Example 34 was changed to "0.45 parts of potassium nonafluorobutane sulfonate". The product was identified by $^1$H-NMR and $^{19}$F-NMR.

(Example 36) Synthesis of [2,5-dimethyl-4-(2-thio-xanthonylthio)phenyl](2,5-dimethylphenyl) (2-thio-xanthonyl)sulfonium Potassium Hexafluorophosphate (P5-P)

[Chem. 43]

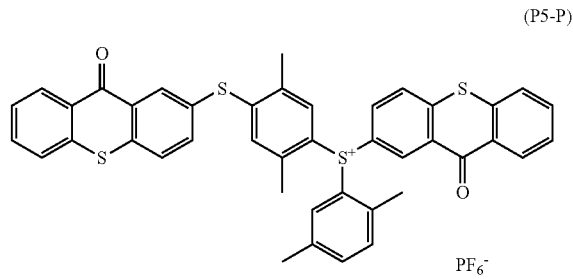
(P5-P)

P5-P in an amount of 0.96 parts was obtained as in Example 34, except that "0.25 parts of potassium trifluoromethane sulfonate" in Example 34 was changed to "0.25 parts of potassium hexafluorophosphate". The product was identified by $^1$H-NMR and $^{19}$F-NMR.

(Example 37) Synthesis of [2,5-dimethyl-4-(2-thio-xanthonylthio)phenyl](2,5-dimethylphenyl) (2-thio-xanthonyl)sulfonium tetrakis(pentafluorophenyl) Borate (P5-B)

[Chem. 44]

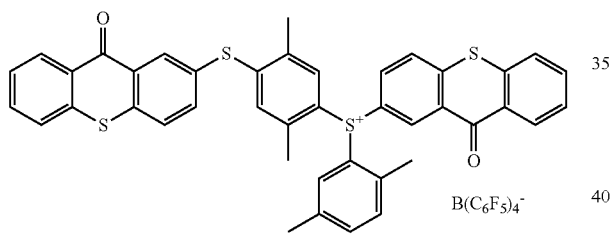
(P5-B)

P5-B in an amount of 1.56 parts was obtained as in Example 34, except that "0.25 parts of potassium trifluoromethane sulfonate" in Example 34 was changed to "0.94 parts of tetrakis(pentafluorophenyl) borate". The product was identified by $^1$H-NMR and $^{19}$F-NMR.

(Example 38) Synthesis of [2,5-dimethyl-4-(2-thio-xanthonylthio)phenyl](2,5-dimethylphenyl) (2-thio-xanthonyl)sulfonium tris(pentafluoroethyl) Trifluorophosphate (P5-FP)

[Chem. 45]

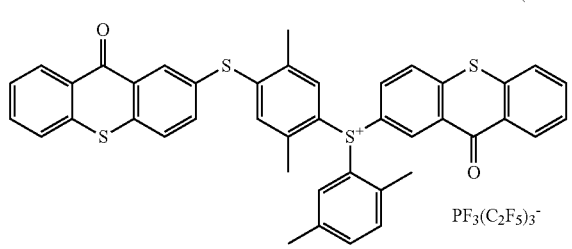
(P5-FP)

P5-FP in an amount of 1.30 parts was obtained as in Example 34, except that "0.25 parts of potassium trifluoromethane sulfonate" in Example 34 was changed to "0.65 parts of potassium tris(pentafluoroethyl) trifluorophosphate". The product was identified by $^1$H-NMR and $^{19}$F-NMR.

(Example 39) Synthesis of [2,5-dimethyl-4-(2-thio-xanthonylthio)phenyl](2,5-dimethylphenyl) (2-thio-xanthonyl)sulfonium Hexafluoroantimonate (P5-SB)

[Chem. 46]

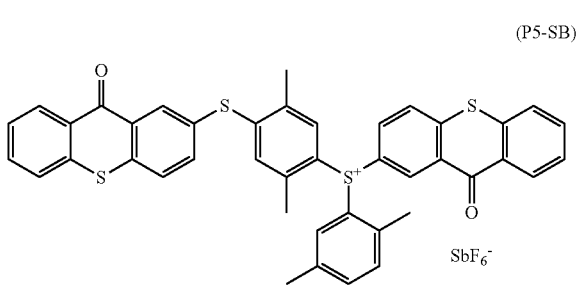
(P5-SB)

P5-SB in an amount of 1.06 parts was obtained as in Example 34, except that "0.25 parts of potassium trifluoromethane sulfonate" in Example 34 was changed to "0.70 parts of potassium hexafluoroantimonate". The product was identified by $^1$H-NMR and $^{19}$F-NMR.

(Example 40) Synthesis of [2,5-dimethyl-4-(2-thio-xanthonylthio)phenyl](2,5-dimethylphenyl) (2-thio-xanthonyl)sulfonium tetrakis(pentafluorophenyl) Gallate (P5-GA)

[Chem. 47]

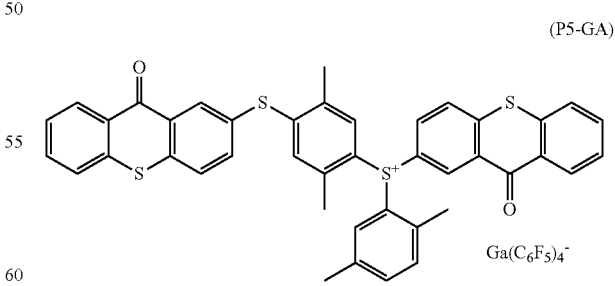
(P5-GA)

P5-GA in an amount of 1.06 parts was obtained as in Example 34, except that "0.25 parts of potassium trifluoromethane sulfonate" in Example 34 was changed to "1.02 parts of sodium tetrakis(pentafluorophenyl) gallate". The product was identified by $^1$H-NMR and $^{19}$F-NMR.

(Example 41) Synthesis of [2-tert-butyl-5-methyl-4-(2-thioxanthonylthio)phenyl](5-tert-butyl-2-methylphenyl) (2-thioxanthonyl)sulfonium Methane Sulfonate (P6-MS)

[Chem. 48]

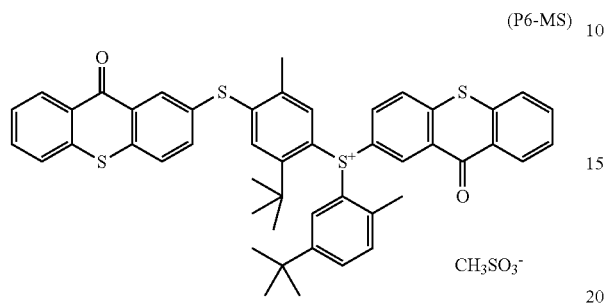

(P6-MS)

An amount of 1.0 part of 2-[(5-tert-butyl-2-methylphenyl)sulfinyl]thioxanthone, 1.0 part of 2-[(5-tert-butyl-2-methylphenyl)thio]thioxanthone, 5.0 parts of acetic anhydride, and 1.9 parts of methanesulfonic acid were homogeneously mixed and reacted at 65° C. for six hours. The reaction solution was cooled to room temperature, poured into 10 parts of ion exchange water, and extracted with 10 parts of dichloromethane. The aqueous phase was removed, and 10 parts of ion exchange water was again fed to wash the organic phase. The organic phase-washing operation was repeated until the pH of the aqueous phase became neutral. Next, unreacted raw materials were eliminated by repeating three times a series of operations involving addition of 15 parts of cyclohexane to the organic phase, stirring, leaving at rest for 30 minutes, and removal of an upper phase. Next, the lower phase was transferred to a rotary evaporator, and the solvent was evaporated. Accordingly, 1.5 parts of a compound (P6-MS) was obtained. The product was identified by $^1$H-NMR and LC-MS.

(Example 42) Synthesis of [2-tert-butyl-5-methyl-4-(2-thioxanthonylthio)phenyl](5-tert-butyl-2-methylphenyl) (2-thioxanthonyl)sulfonium Trifluoromethane Sulfonate (P6-TF)

[Chem. 49]

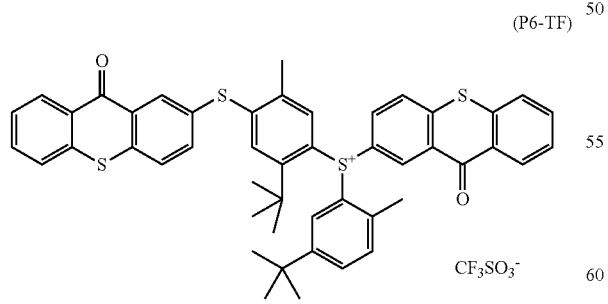

(P6-TF)

The [2-tert-butyl-5-methyl-4-(2-thioxanthonylthio)phenyl](5-tert-butyl-2-methylphenyl) (2-thioxanthonyl)sulfonium methane sulfonate (P6-MS) synthesized in Example 41 in an amount of 1.0 part was dissolved in 5.8 parts of dichloromethane. To the solution were added 0.23 parts of potassium trifluoromethane sulfonate and 5.1 parts of ion exchange water, followed by stirring at room temperature for one hour. Subsequently, the organic phase was washed with 5 parts of ion exchange water five times. Next, the organic phase was transferred to a rotary evaporator, and the solvent was evaporated. Accordingly, 0.96 parts of P6-TF was obtained. The product was identified by $^1$H-NMR and $^{19}$F-NMR.

(Example 43) Synthesis of [2-tert-butyl-5-methyl-4-(2-thioxanthonylthio)phenyl](5-tert-butyl-2-methylphenyl) (2-thioxanthonyl)sulfonium Nonafluorobutane Sulfonate (P6-NF)

[Chem. 50]

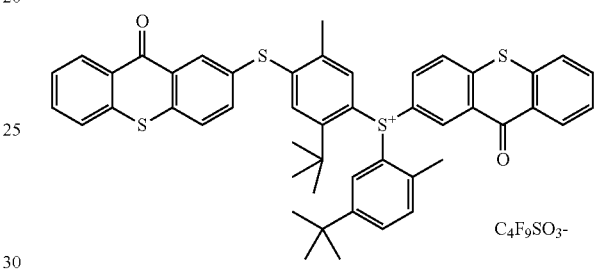

(P6-NF)

P6-NF in an amount of 1.1 parts was obtained as in Example 42, except that "0.23 parts of potassium trifluoromethane sulfonate" in Example 42 was changed to "0.41 parts of potassium nonafluorobutane sulfonate". The product was identified by $^1$H-NMR and $^{19}$F-NMR.

(Example 44) Synthesis of [2-tert-butyl-5-methyl-4-(2-thioxanthonylthio)phenyl](5-tert-butyl-2-methylphenyl) (2-thioxanthonyl)sulfonium Hexafluorophosphate (P6-P)

[Chem. 51]

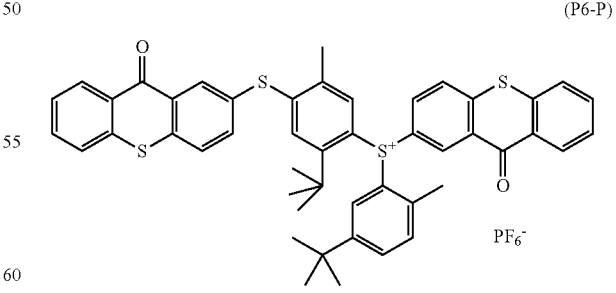

(P6-P)

P6-NF in an amount of 0.95 parts was obtained as in Example 42, except that "0.23 parts of potassium trifluoromethane sulfonate" in Example 42 was changed to "0.22 parts of potassium hexafluorophosphate". The product was identified by $^1$H-NMR and $^{19}$F-NMR.

(Example 45) Synthesis of [2-tert-butyl-5-methyl-4-(2-thioxanthonylthio)phenyl](5-tert-butyl-2-methylphenyl) (2-thioxanthonyl)sulfonium tetrakis(pentafluorophenyl) Borate (P6-B)

[Chem. 52]

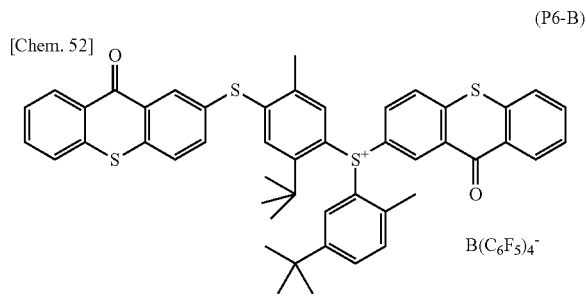

(P6-B)

P6-B in an amount of 1.5 parts was obtained as in Example 42, except that "0.23 parts of potassium trifluoromethane sulfonate" in Example 42 was changed to "0.85 parts of sodium tetrakis(pentafluorophenyl) borate". The product was identified by $^1$H-NMR and $^{19}$F-NMR.

(Example 46) Synthesis of [2-tert-butyl-5-methyl-4-(2-thioxanthonylthio)phenyl](5-tert-butyl-2-methylphenyl) (2-thioxanthonyl)sulfonium tris(pentafluoroethyl) Trifluorophosphate (P6-FP)

[Chem. 53]

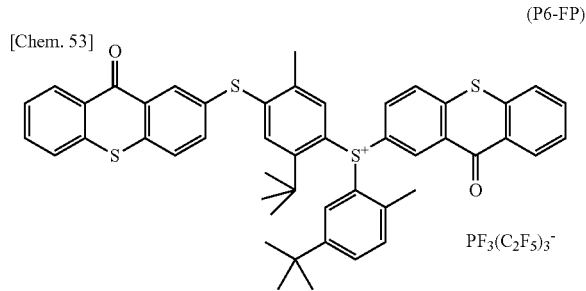

(P6-FP)

P6-FP in an amount of 1.26 parts was obtained as in Example 42, except that "0.23 parts of potassium trifluoromethane sulfonate" in Example 42 was changed to "0.59 parts of potassium tris(pentafluoroethyl) trifluorophosphate". The product was identified by $^1$H-NMR and $^{19}$F-NMR.

(Example 47) Synthesis of [2-tert-butyl-5-methyl-4-(2-thioxanthonylthio)phenyl](5-tert-butyl-2-methylphenyl) (2-thioxanthonyl)sulfonium Hexafluoroantimonate (P6-SB)

[Chem. 54]

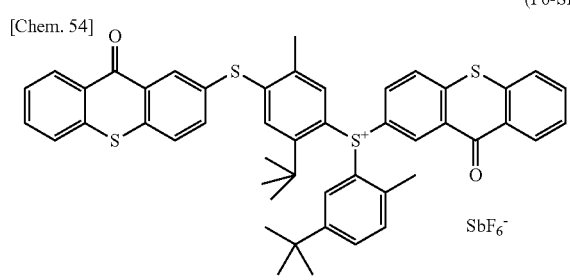

(P6-SB)

P6-SB in an amount of 1.05 parts was obtained as in Example 42, except that "0.23 parts of potassium trifluoromethane sulfonate" in Example 42 was changed to "0.63 parts of potassium hexafluoroantimonate". The product was identified by $^1$H-NMR and $^{19}$F-NMR.

(Example 48) Synthesis of [2-tert-butyl-5-methyl-4-(2-thioxanthonylthio)phenyl](5-tert-butyl-2-methylphenyl) (2-thioxanthonyl)sulfonium tetrakis(pentafluorophenyl) Gallate (P6-GA)

[Chem. 55]

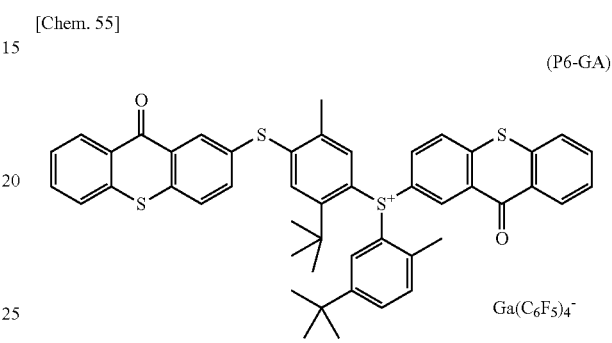

(P6-GA)

P6-GA in an amount of 1.56 parts was obtained as in Example 42, except that "0.23 parts of potassium trifluoromethane sulfonate" in Example 42 was changed to "0.92 parts of sodium tetrakis(pentafluorophenyl) gallate". The product was identified by $^1$H-NMR and $^{19}$F-NMR.

(Example 49) Synthesis of [2,5-dimethyl-4-(2-thioxanthonyloxy)phenyl](2,5-dimethylphenyl) (2-thioxanthonyl)sulfonium tris(pentafluoroethyl) Trifluorophosphate (P7-FP)

[Chem. 56]

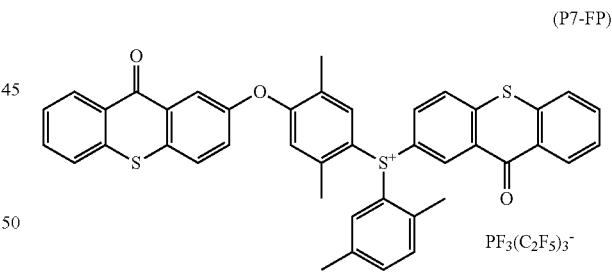

(P7-FP)

An amount of 1.0 part of 2-[(2,5-dimethylphenyl)sulfinyl]thioxanthone, 1.1 parts of 2-[(2,5-dimethylphenyl)oxy]thioxanthone, 6.5 parts of acetic anhydride, and 3.0 parts of methanesulfonic acid were homogeneously mixed and reacted at 65° C. for 12 hours. The reaction solution was cooled to room temperature, poured into 15 parts of ion exchange water, and extracted with 15 parts of dichloromethane. The aqueous phase was removed, and 0.6 parts of potassium tris(pentafluoroethyl) trifluorophosphate and 15 parts of ion exchange water were added. They were stirred at room temperature for one hour. The aqueous phase was removed, and 15 parts of ion exchange water was fed to wash the organic phase. The organic phase-washing operation was repeated until the pH of the aqueous phase became neutral. Next, unreacted raw materials were eliminated by repeating five times a series of operations involving addition of 20 parts of cyclohexane to the organic phase, stirring, leaving at rest for 30 minutes, and removal of an upper phase. Next, the lower phase was transferred to a rotary evaporator, and the solvent was evaporated. Accordingly, 0.6 parts of a compound (P7-FP) was obtained. The product was identified by $^1$H-NMR, $^{19}$F-NMR, and LC-MS.

(Example 50) Synthesis of [2,5-dimethyl-4-(2-thioxanthonylsulfinyl)phenyl](2,5-dimethylphenyl)(2-thioxanthonyl)sulfonium tris(pentafluoroethyl) Trifluorophosphate (P8-FP)

[Chem. 57]

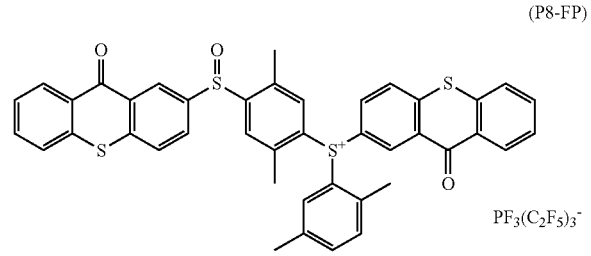

(P8-FP)

PF$_3$(C$_2$F$_5$)$_3^-$

The sulfonium salt P5-FP obtained in Example 38 in an amount of 1.0 part, 4 parts of acetonitrile, 0.01 parts of sulfuric acid, and 0.09 parts of 35% hydrogen peroxide water were homogeneously mixed and reacted at 50° C. for three hours. The reaction solution was cooled to room temperature, fed with 10 parts of ion exchange water, and extracted with 5 parts of dichloromethane. The aqueous phase was removed, and 10 parts of ion exchange water was again fed to wash the organic phase. The washing operation was repeated until the pH became neutral. Next, the organic phase was transferred to a rotary evaporator, and the solvent was evaporated. Accordingly, 1.0 part of a compound P8-FP was obtained. The product was identified by $^1$H-NMR, $^{19}$F-NMR, and LC-MS.

(Example 51) Synthesis of [2,5-dimethyl-4-(2-thioxanthonylsulfonyl)phenyl](2,5-dimethylphenyl)(2-thioxanthonyl)sulfonium tris(pentafluoroethyl) Trifluorophosphate (P9-FP)

[Chem. 58]

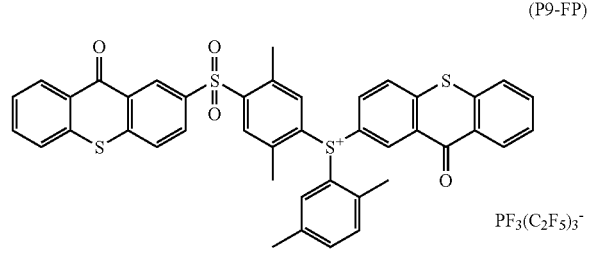

(P9-FP)

PF$_3$(C$_2$F$_5$)$_3^-$

The sulfonium salt P5-FP obtained in Example 38 in an amount of 1.0 part, 4 parts of acetonitrile, 0.01 parts of sulfuric acid, and 0.2 parts of 35% hydrogen peroxide water were homogeneously mixed and reacted at 80° C. for five hours. The reaction solution was cooled to room temperature, fed with 10 parts of ion exchange water, and extracted with 5 parts of dichloromethane. The aqueous phase was removed, and 10 parts of ion exchange water was again fed to wash the organic phase. The washing operation was repeated until the pH became neutral. Next, the organic phase was transferred to a rotary evaporator, and the solvent was evaporated. Accordingly, 1.0 part of a compound P9-FP was obtained. The product was identified by $^1$H-NMR, $^{19}$F-NMR, and LC-MS.

(Comparative Example 1) Synthesis of Compound H1-TF

[Chem. 59]

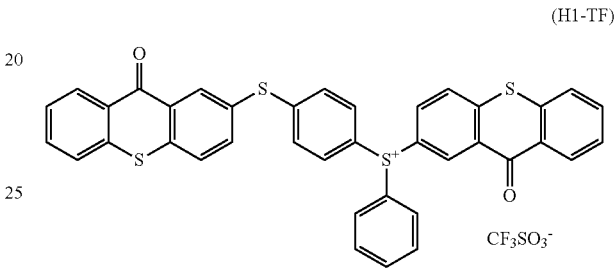

(H1-TF)

CF$_3$SO$_3^-$

While 4.3 parts of 2-(phenylthio)thioxanthone, 4.5 parts of 2-[(phenyl)sulfinyl]thioxanthone, 4.1 parts of acetic anhydride, and 110 parts of acetonitrile were stirred at 40° C., 2.4 parts of trifluoromethanesulfonic acid was gradually dropwise added thereto. They were reacted at 40° C. to 45° C. for one hour. The reaction solution was cooled to room temperature (about 25° C.), poured into 150 parts of distilled water, extracted with chloroform, and washed with water until the pH of the aqueous phase became neutral. The chloroform phase was transferred to a rotary evaporator, and the solvent was evaporated. The solid formed was washed by repeating three times a series of operations involving addition of 50 parts of toluene, dispersion in the toluene using an ultrasonic washer, leaving at rest for about 15 minutes, and removal of a supernatant. Then, the solid was transferred to a rotary evaporator, and the solvent was evaporated. Accordingly, H1-TF was obtained.

(Comparative Example 2) Synthesis of Compound H1-P

[Chem. 60]

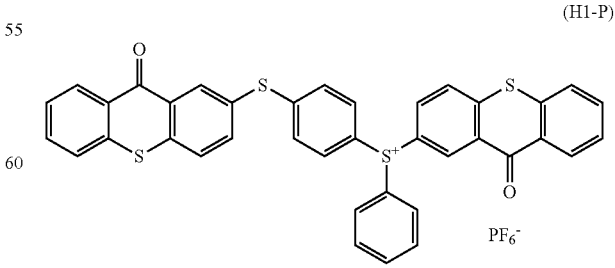

(H1-P)

PF$_6^-$

The H1-TF in an amount of 1.0 part was dissolved in 6.4 parts of dichloromethane. To the solution were added 0.25 parts of potassium hexafluorophosphate and 5.7 parts of ion exchange water, followed by stirring at room temperature for one hour. Subsequently, the organic phase was washed with 6 parts of ion exchange water five times. The organic phase was transferred to a rotary evaporator, and the solvent was evaporated. Accordingly, 0.96 parts of H1-P was obtained. The product was identified by $^1$H-NMR and $^{19}$F-NMR.

(Comparative Example 3) Synthesis of Compound H1-FP

[Chem. 61]

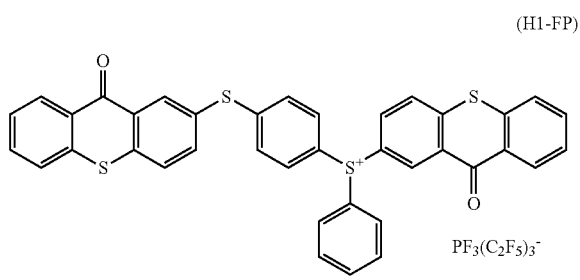

(H1-FP)

PF$_3$(C$_2$F$_5$)$_3^-$

H1-FP in an amount of 1.2 parts was obtained as in Comparative Example 2, except that "0.25 parts of potassium hexafluorophosphate" in Comparative Example 2 was changed to "0.60 parts of potassium tris(pentafluoroethyl) trifluorophosphate". The product was identified by $^1$H-NMR and $^{19}$F-NMR.

(Comparative Example 4) Synthesis of Compound H1-SB

[Chem. 62]

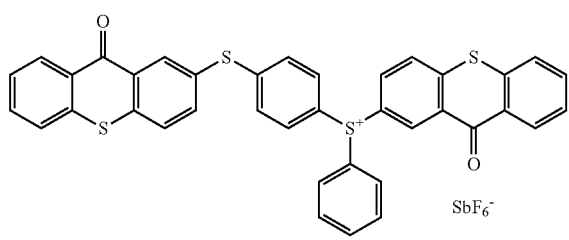

(H1-SB)

SbF$_6^-$

H1-SB in an amount of 1.0 part was obtained as in Comparative Example 2, except that "0.25 parts of potassium hexafluorophosphate" in Comparative Example 2 was changed to "0.63 parts of potassium hexafluoroantimonate". The product was identified by $^1$H-NMR and $^{19}$F-NMR.

[Preparation and Evaluation of Energy Ray-Curable Composition]

<Preparation of Curable Composition>

Energy ray-curable compositions (Examples C1 to C33, Comparative Examples HC1 to HC3) were each prepared by homogeneously mixing the photoacid generator (sulfonium salt) of the present invention or a photoacid generator (sulfonium salt) of a comparative example with an epoxide (3,4-epoxycyclohexylmethyl-3,4-epoxycyclohexane carboxylate, Daicel Corporation, Celloxide 2021P) as a cationically polymerizable compound in amounts (parts by weight) indicated in Table 1.

TABLE 1

| | Example of corresponding photoacid generator | Amount of photoacid generator | Epoxide |
|---|---|---|---|
| Example | | | |
| C1 | Example 4 | 1.00 | 100 |
| C2 | Example 5 | 0.20 | 100 |
| C3 | Example 6 | 0.20 | 100 |
| C4 | Example 7 | 0.20 | 100 |
| C5 | Example 8 | 0.20 | 100 |
| C6 | Example 12 | 1.00 | 100 |
| C7 | Example 13 | 0.20 | 100 |
| C8 | Example 14 | 0.20 | 100 |
| C9 | Example 15 | 0.20 | 100 |
| C10 | Example 16 | 0.20 | 100 |
| C11 | Example 20 | 1.00 | 100 |
| C12 | Example 21 | 0.20 | 100 |
| C13 | Example 22 | 0.20 | 100 |
| C14 | Example 23 | 0.20 | 100 |
| C15 | Example 24 | 0.20 | 100 |
| C16 | Example 28 | 1.00 | 100 |
| C17 | Example 29 | 0.20 | 100 |
| C18 | Example 30 | 0.20 | 100 |
| C19 | Example 31 | 0.20 | 100 |
| C20 | Example 32 | 0.20 | 100 |
| C21 | Example 36 | 1.00 | 100 |
| C22 | Example 37 | 0.20 | 100 |
| C23 | Example 38 | 0.20 | 100 |
| C24 | Example 39 | 0.20 | 100 |
| C25 | Example 40 | 0.20 | 100 |
| C26 | Example 44 | 1.00 | 100 |
| C27 | Example 45 | 0.20 | 100 |
| C28 | Example 46 | 0.20 | 100 |
| C29 | Example 47 | 0.20 | 100 |
| C30 | Example 48 | 0.20 | 100 |
| C31 | Example 49 | 0.20 | 100 |
| C32 | Example 50 | 0.20 | 100 |
| C33 | Example 51 | 0.20 | 100 |
| Comparative Example | | | |
| HCC | Comparative Example 2 | 1.00 | 100 |
| HC2 | Comparative Example 3 | 0.20 | 100 |
| HC3 | Comparative Example 4 | 0.20 | 100 |

The sulfonium salts prepared in Example 4, Example 12, Example 20, Example 28, Example 36, Examples 44, and Comparative Example 2 are hexafluorophosphates which generate acids having a lower acid strength and thus less active in cationic polymerization than those generated by tetrakis(pentafluorophenyl) borate, tris(pentafluoroethyl) trifluorophosphate, hexafluoroantimonate, and tetrakis(pentafluorophenyl) gallate prepared in Examples 5 to 8, Examples 13 to 16, Examples 21 to 24, Examples 29 to 32, Examples 37 to 40, Examples 45 to 51, and Comparative Examples 3 and 4. Therefore, the sulfonium salts were used in larger amounts.

<Photosensitivity (Photocurability) Evaluation>

The energy ray-curable composition obtained above was applied to a polyethylene terephthalate (PET) film sheet with an applicator (40 µm). Using an ultraviolet irradiator, the PET film sheet was exposed to ultraviolet light, the wavelength of which was restricted with a filter. The filter used was L-39 (Kenko Optical Co., Ltd., a filter for cutting off light with wavelengths of 390 nm or less). Forty minutes after the exposure, the hardness of the coating film in terms of pencil hardness (JIS K 5600-5-4: 1999) was measured and evaluated according to the criteria below (the coating film had a thickness of about 40 μm after curing). Table 2 shows the results. A higher pencil hardness indicates better photocurability of the energy ray-curable composition. Specifically, the sulfonium salt has an excellent ability to initiate polymerization (photosensitivity of the sulfonium salt) of the cationically polymerizable compound.

(Evaluation Criteria)
Very good (∘∘): The pencil hardness is H or higher.
Good (∘): The pencil hardness is from HB to B.
Fair (Δ): The pencil hardness is from 2B to 4B.
Bad (x): It is impossible to measure the pencil hardness due to liquidness or tacks.

(Ultraviolet Light Irradiation Conditions)
  Ultraviolet light irradiator: belt conveyor-type UV irradiator (Eye Graphics Co., Ltd.)
  Lamp: 1.5 kW high-pressure mercury lamp
  Filter: L-39 (Kenko Optical Co., Ltd., filter for cutting off light with wavelengths of 390 nm or less)
  Irradiance (measured with a 405 nm-head photometer): 80 mW/cm$^2$
  Integral light dose (measured with a 405 nm-head photometer):
    Condition-1: 50 mJ/cm$^2$
    Condition-2: 100 mJ/cm$^2$
    Condition-3: 150 mJ/cm$^2$ <Storage Stability>
The energy ray-curable composition obtained above was stored under shading and heating at 80° C. for one month. The viscosities of the composition sample before and after the heating were measured. The storage stability was evaluated based on the following criteria. A lower viscosity increase indicates better storage stability.

(Evaluation Criteria)
Bad (x): The viscosity increased by 1.5 times or more from before to after heating.
Good (∘): The viscosity increased by less than 1.5 times from before to after heating.

TABLE 2

|  | Photocurability | | | Storage |
| --- | --- | --- | --- | --- |
|  | Condition-1 | Condition-2 | Condition-3 | stability |
| Example |  |  |  |  |
| C1 | ∘ | ∘ | ∘∘ | ∘ |
| C2 | ∘ | ∘ | ∘∘ | ∘ |
| C3 | ∘ | ∘ | ∘∘ | ∘ |
| C4 | ∘ | ∘ | ∘∘ | ∘ |
| C5 | ∘ | ∘ | ∘∘ | ∘ |
| C6 | ∘ | ∘ | ∘∘ | ∘ |
| C7 | ∘ | ∘ | ∘∘ | ∘ |
| C8 | ∘ | ∘ | ∘∘ | ∘ |
| C9 | ∘ | ∘ | ∘∘ | ∘ |
| C10 | ∘ | ∘ | ∘∘ | ∘ |
| C11 | ∘ | ∘∘ | ∘∘ | ∘ |
| C12 | ∘ | ∘∘ | ∘∘ | ∘ |
| C13 | ∘ | ∘∘ | ∘∘ | ∘ |
| C14 | ∘ | ∘∘ | ∘∘ | ∘ |
| C15 | ∘ | ∘∘ | ∘∘ | ∘ |
| C16 | ∘ | ∘∘ | ∘∘ | ∘ |
| C17 | ∘ | ∘∘ | ∘∘ | ∘ |
| C18 | ∘ | ∘∘ | ∘∘ | ∘ |
| C19 | ∘ | ∘∘ | ∘∘ | ∘ |
| C20 | ∘ | ∘∘ | ∘∘ | ∘ |
| C21 | ∘ | ∘∘ | ∘∘ | ∘ |
| C22 | ∘ | ∘∘ | ∘∘ | ∘ |
| C23 | ∘ | ∘∘ | ∘∘ | ∘ |
| C24 | ∘ | ∘∘ | ∘∘ | ∘ |
| C25 | ∘ | ∘∘ | ∘∘ | ∘ |
| C26 | ∘ | ∘∘ | ∘∘ | ∘ |
| C27 | ∘ | ∘∘ | ∘∘ | ∘ |
| C28 | ∘ | ∘∘ | ∘∘ | ∘ |
| C29 | ∘ | ∘∘ | ∘∘ | ∘ |
| C30 | ∘ | ∘∘ | ∘∘ | ∘ |
| C31 | ∘ | ∘∘ | ∘∘ | ∘ |
| C32 | ∘ | ∘∘ | ∘∘ | ∘ |
| C33 | ∘ | ∘∘ | ∘∘ | ∘ |
| Comparative Example |  |  |  |  |
| HC1 | x | Δ | ∘ | ∘ |
| HC2 | x | Δ | ∘ | ∘ |
| HC3 | x | Δ | ∘ | ∘ |

As demonstrated by the results in Table 2, the photoacid generator of the present invention has a better ability (photosensitivity) to cure the cationically polymerizable compound with ultraviolet light at 405 nm or higher than the comparative photoacid generators. When the substituent R5 is bulkier or the number n of R5 is larger in the formula (1), better curability is exhibited.

[Evaluation of Chemically Amplifiable Positive Photoresist Composition]

<Preparation of Evaluation Sample>
The component (A) as a photoacid generator in an amount of 1 part by weight, 40 parts by weight of a resin represented by the following formula (Resin-1) as the resin (B), and 60 parts by weight of a novolac resin as the resin (C) obtained by addition condensation of m-cresol and p-cresol in the presence of formaldehyde and an acid catalyst as indicated in Table 3 were uniformly dissolved in a solvent-1 (propylene glycol monomethylether acetate). The resulting solution was filtered through a membrane filter with a pore size of 1 μm. Thus, chemically amplifiable positive photoresist compositions having a solid concentration of 40% by weight were prepared (Examples P1 to P39).

Chemically amplifiable positive photoresist compositions of comparative examples (Comparative Examples HP1 to HP4) were prepared as above using the components in the amounts indicated in Table 3.

TABLE 3

| Example | Example of corresponding photoacid generator (A) | Amount of photoacid generator (A) | Resin (B) | Resin (C) | Solvent-1 |
| --- | --- | --- | --- | --- | --- |
| P1 | Example 1 | 1 | 40 | 60 | 151.5 |
| P2 | Example 2 | 1 | 40 | 60 | 151.5 |
| P3 | Example 3 | 1 | 40 | 60 | 151.5 |
| P4 | Example 5 | 1 | 40 | 60 | 151.5 |
| P5 | Example 6 | 1 | 40 | 60 | 151.5 |
| P6 | Example 8 | 1 | 40 | 60 | 151.5 |
| P7 | Example 9 | 1 | 40 | 60 | 151.5 |
| P8 | Example 10 | 1 | 40 | 60 | 151.5 |
| P9 | Example 11 | 1 | 40 | 60 | 151.5 |
| P10 | Example 13 | 1 | 40 | 60 | 151.5 |
| P11 | Example 14 | 1 | 40 | 60 | 151.5 |
| P12 | Example 16 | 1 | 40 | 60 | 151.5 |
| P13 | Example 17 | 1 | 40 | 60 | 151.5 |
| P14 | Example 18 | 1 | 40 | 60 | 151.5 |
| P15 | Example 19 | 1 | 40 | 60 | 151.5 |
| P16 | Example 21 | 1 | 40 | 60 | 151.5 |
| P17 | Example 22 | 1 | 40 | 60 | 151.5 |
| P18 | Example 24 | 1 | 40 | 60 | 151.5 |
| P19 | Example 25 | 1 | 40 | 60 | 151.5 |
| P20 | Example 26 | 1 | 40 | 60 | 151.5 |

TABLE 3-continued

| Example | Example of corresponding photoacid generator (A) | Amount of photoacid generator (A) | Resin (B) | Resin (C) | Solvent-1 |
|---|---|---|---|---|---|
| P21 | Example 27 | 1 | 40 | 60 | 151.5 |
| P22 | Example 29 | 1 | 40 | 60 | 151.5 |
| P23 | Example 30 | 1 | 40 | 60 | 151.5 |
| P24 | Example 32 | 1 | 40 | 60 | 151.5 |
| P25 | Example 33 | 1 | 40 | 60 | 151.5 |
| P26 | Example 34 | 1 | 40 | 60 | 151.5 |
| P27 | Example 35 | 1 | 40 | 60 | 151.5 |
| P28 | Example 37 | 1 | 40 | 60 | 151.5 |
| P29 | Example 38 | 1 | 40 | 60 | 151.5 |
| P30 | Example 40 | 1 | 40 | 60 | 151.5 |
| P31 | Example 41 | 1 | 40 | 60 | 151.5 |
| P32 | Example 42 | 1 | 40 | 60 | 151.5 |
| P33 | Example 43 | 1 | 40 | 60 | 151.5 |
| P34 | Example 45 | 1 | 40 | 60 | 151.5 |
| P35 | Example 46 | 1 | 40 | 60 | 151.5 |
| P36 | Example 48 | 1 | 40 | 60 | 151.5 |
| P37 | Example 49 | 1 | 40 | 60 | 151.5 |
| P38 | Example 50 | 1 | 40 | 60 | 151.5 |
| P39 | Example 51 | 1 | 40 | 60 | 151.5 |
| Comparative Example | | | | | |
| HP1 | Comparative Example 1 | 1 | 40 | 60 | 151.5 |
| HP2 | Comparative Example 3 | 1 | 40 | 60 | 151.5 |
| HP3 | Ref-1 | 1 | 40 | 60 | 151.5 |
| HP4 | Ref-2 | 1 | 40 | 60 | 151.5 |

[Chem. 63]

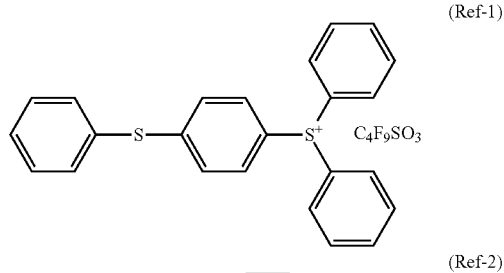

(Ref-1)

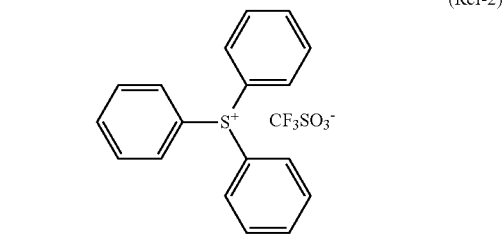

(Ref-2)

[Chem. 64]

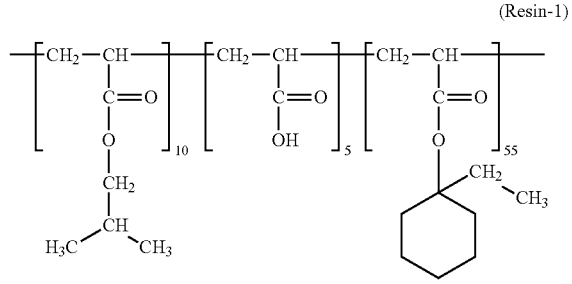

(Resin-1)

<Sensitivity Evaluation>

The positive resist compositions prepared in Examples P1 to P36 and Comparative Examples HP1 to HP4 were each spin-coated on a silicon wafer substrate and dried, thereby preparing a photoresist layer having a thickness of about 20 µm. The resist layer was pre-baked on a hot plate at 130° C. for six minutes. After pre-baking, pattern exposure (i-rays) was performed using TME-150RSC (TOPCON CORPORATION), followed by post-exposure baking (PEB) using a hot plate at 75° C. for five minutes. Subsequently, development was performed for five minutes by an immersion method using a 2.38% by weight aqueous solution of tetramethyl ammonium hydroxide. The workpiece was washed with running water and then subjected to nitrogen blowing, thereby forming a 10 µm line-and-space (L&S) pattern. Next, a minimum exposure dose under which no pattern remains, i.e., a minimum required exposure dose (corresponding to sensitivity) needed to form a resist pattern, was measured. A lower required exposure dose indicates better photoreactivity of the positive resist composition; in other words, the sulfonium salt has better photosensitivity.

<Storage Stability Evaluation>

The photosensitivity (sensitivity) of the chemically amplifiable positive resist composition immediately after preparation and the photosensitivity after one month storage at 40° C. were analyzed as above. The storage stability was evaluated based on the following criteria.

Good (○): The difference between the sensitivity after one month storage at 40° C. and the sensitivity immediately after preparation is less than 5%.

Bad (x): The difference between the sensitivity after one month storage at 40° C. and the sensitivity immediately after preparation is 5% or more.

<Pattern Shape Evaluation>

The cross-sectional shape of the 10 µm-thick L&S pattern formed on the silicon wafer substrate by the above operation was observed with a scanning electron microscope to measure the length La of the lower side and the length Lb of the upper side. The pattern shape was evaluated based on the following criteria. Table 4 shows the results.

Very good (○○): 0.90≤Lb/La≤1
Good (○): 0.85≤Lb/La<0.90
Bad (x): Lb/La<0.85

TABLE 4

| Example | Example of corresponding photoacid generator (A) | Minimum required exposure dose (mJ/cm²) | Storage stability | Pattern shape |
|---|---|---|---|---|
| P1 | Example 1 | 170 | ○ | ○ |
| P2 | Example 2 | 160 | ○ | ○ |
| P3 | Example 3 | 160 | ○ | ○ |
| P4 | Example 5 | 150 | ○ | ○ |
| P5 | Example 6 | 150 | ○ | ○ |
| P6 | Example 8 | 150 | ○ | ○ |
| P7 | Example 9 | 160 | ○ | ○ |
| P8 | Example 10 | 150 | ○ | ○ |
| P9 | Example 11 | 150 | ○ | ○ |
| P10 | Example 13 | 140 | ○ | ○ |
| P11 | Example 14 | 140 | ○ | ○ |
| P12 | Example 16 | 140 | ○ | ○ |
| P13 | Example 17 | 150 | ○ | ○ |
| P14 | Example 18 | 140 | ○ | ○ |
| P15 | Example 19 | 140 | ○ | ○ |
| P16 | Example 21 | 130 | ○ | ○ |
| P17 | Example 22 | 130 | ○ | ○ |
| P18 | Example 24 | 130 | ○ | ○ |
| P19 | Example 25 | 150 | ○ | ○ |
| P20 | Example 26 | 140 | ○ | ○ |

TABLE 4-continued

| Example | Example of corresponding photoacid generator (A) | Minimum required exposure dose (mJ/cm$^2$) | Storage stability | Pattern shape |
|---|---|---|---|---|
| P21 | Example 27 | 140 | ○ | ○ |
| P22 | Example 29 | 130 | ○ | ○ |
| P23 | Example 30 | 130 | ○ | ○ |
| P24 | Example 32 | 130 | ○ | ○ |
| P25 | Example 33 | 150 | ○ | ○ |
| P26 | Example 34 | 140 | ○ | ○ |
| P27 | Example 35 | 140 | ○ | ○ |
| P28 | Example 37 | 130 | ○ | ○ |
| P29 | Example 38 | 130 | ○ | ○ |
| P30 | Example 40 | 130 | ○ | ○ |
| P31 | Example 41 | 150 | ○ | ○ |
| P32 | Example 42 | 140 | ○ | ○ |
| P33 | Example 43 | 140 | ○ | ○ |
| P34 | Example 45 | 130 | ○ | ○ |
| P35 | Example 46 | 130 | ○ | ○ |
| P36 | Example 48 | 130 | ○ | ○ |
| P37 | Example 49 | 130 | ○ | ○ |
| P38 | Example 50 | 130 | ○ | ○ |
| P39 | Example 51 | 130 | ○ | ○ |
| Comparative Example | | | | |
| HP1 | Comparative Example 1 | 200 | ○ | ○ |
| HP2 | Comparative Example 3 | 180 | ○ | ○ |
| HP3 | Ref-1 | 1100 | ○ | ○ |
| HP4 | Ref-2 | 5000 or more | — | — |

Note)
—: The storage stability was not evaluated because the minimum required exposure dose could not be specified.

As demonstrated in Table 4, the chemically amplifiable positive photoresist compositions of Examples P1 to P39 have a higher sensitivity than those using conventional photoacid generators in Comparative Examples HP1 to HP4, and are excellent in storage stability and pattern shapes. When the substituent R5 is bulkier or the number n of R5 is larger in the formula (1), better photosensitivity is exhibited, and the corresponding positive photoresist compositions have a higher sensitivity.

[Evaluation of Chemically Amplifiable Negative Photoresist Composition]

<Preparation of Evaluation Sample>

As indicated in Table 5, the component (E) as a photoacid generator in an amount of 1.0 parts by weight, 100 parts by weight of a copolymer (Mw=10,000) having a molar ratio of p-hydroxystyrene/styrene of 80/20 which is a phenolic resin as the component (F), 20 parts by weight of hexamethoxymethyl melamine (Sanwa Chemical Co., Ltd., trade name "NIKALAC MW-390") which is a crosslinking agent as the component (G), 10 parts by weight of a copolymer (average particle size=65 nm, Tg=−38° C.) having a ratio of butadiene/acrylonitrile/hydroxybutyl methacrylate/methacrylic acid/divinylbenzene of 64/20/8/6/2 (% by weight), which is crosslinked fine particles as the component (H), and 5 parts by weight of γ-glycidoxypropyltrimethoxysilane (Chisso Corporation, trade name "S510") which is an adhesion aid as the component (I) were uniformly dissolved in 145 parts by weight of a solvent-2 (ethyl lactate). Thus, chemically amplifiable negative photoresist compositions of the present invention were prepared (Examples N1 to N39).

Chemically amplifiable negative photoresist compositions of comparative examples (Comparative Examples HN1 to HN4) were prepared as above using the components in the amounts indicated in Table 5.

TABLE 5

| Example | Example of corresponding photoacid generator (E) | Amount of photoacid generator (E) | Resin (F) | Resin (G) | Crosslinking fine particles (H) | Adhesion aid (I) | Solvent-2 |
|---|---|---|---|---|---|---|---|
| N1 | Example 1 | 1 | 100 | 20 | 10 | 5 | 145 |
| N2 | Example 2 | 1 | 100 | 20 | 10 | 5 | 145 |
| N3 | Example 3 | 1 | 100 | 20 | 10 | 5 | 145 |
| N4 | Example 5 | 1 | 100 | 20 | 10 | 5 | 145 |
| N5 | Example 6 | 1 | 100 | 20 | 10 | 5 | 145 |
| N6 | Example 8 | 1 | 100 | 20 | 10 | 5 | 145 |
| N7 | Example 9 | 1 | 100 | 20 | 10 | 5 | 145 |
| N8 | Example 10 | 1 | 100 | 20 | 10 | 5 | 145 |
| N9 | Example 11 | 1 | 100 | 20 | 10 | 5 | 145 |
| N10 | Example 13 | 1 | 100 | 20 | 10 | 5 | 145 |
| N11 | Example 14 | 1 | 100 | 20 | 10 | 5 | 145 |
| N12 | Example 16 | 1 | 100 | 20 | 10 | 5 | 145 |
| N13 | Example 17 | 1 | 100 | 20 | 10 | 5 | 145 |
| N14 | Example 18 | 1 | 100 | 20 | 10 | 5 | 145 |
| N15 | Example 19 | 1 | 100 | 20 | 10 | 5 | 145 |
| N16 | Example 21 | 1 | 100 | 20 | 10 | 5 | 145 |
| N17 | Example 22 | 1 | 100 | 20 | 10 | 5 | 145 |
| N18 | Example 24 | 1 | 100 | 20 | 10 | 5 | 145 |
| N19 | Example 25 | 1 | 100 | 20 | 10 | 5 | 145 |
| N20 | Example 26 | 1 | 100 | 20 | 10 | 5 | 145 |
| N21 | Example 27 | 1 | 100 | 20 | 10 | 5 | 145 |
| N22 | Example 29 | 1 | 100 | 20 | 10 | 5 | 145 |
| N23 | Example 30 | 1 | 100 | 20 | 10 | 5 | 145 |
| N24 | Example 32 | 1 | 100 | 20 | 10 | 5 | 145 |
| N25 | Example 33 | 1 | 100 | 20 | 10 | 5 | 145 |
| N26 | Example 34 | 1 | 100 | 20 | 10 | 5 | 145 |
| N27 | Example 35 | 1 | 100 | 20 | 10 | 5 | 145 |
| N28 | Example 37 | 1 | 100 | 20 | 10 | 5 | 145 |
| N29 | Example 38 | 1 | 100 | 20 | 10 | 5 | 145 |
| N30 | Example 40 | 1 | 100 | 20 | 10 | 5 | 145 |
| N31 | Example 41 | 1 | 100 | 20 | 10 | 5 | 145 |
| N32 | Example 42 | 1 | 100 | 20 | 10 | 5 | 145 |

TABLE 5-continued

| Example | Example of corresponding photoacid generator (E) | Amount of photoacid generator (E) | Resin (F) | Resin (G) | Crosslinking fine particles (H) | Adhesion aid (I) | Solvent-2 |
|---|---|---|---|---|---|---|---|
| N33 | Example 43 | 1 | 100 | 20 | 10 | 6 | 145 |
| N34 | Example 45 | 1 | 100 | 20 | 10 | 5 | 145 |
| N35 | Example 46 | 1 | 100 | 20 | 10 | 5 | 145 |
| N36 | Example 48 | 1 | 100 | 20 | 10 | 5 | 145 |
| N37 | Example 49 | 1 | 100 | 20 | 10 | 5 | 145 |
| N38 | Example 50 | 1 | 100 | 20 | 10 | 5 | 145 |
| N39 | Example 51 | 1 | 100 | 20 | 10 | 5 | 145 |
| Comparative Example | | | | | | | |
| HN1 | Comparative Example 1 | 1 | 100 | 20 | 10 | 5 | 145 |
| HN2 | Comparative Example 3 | 1 | 100 | 20 | 10 | 5 | 145 |
| HN3 | Ref-1 | 1 | 100 | 20 | 10 | 5 | 145 |
| HN4 | Ref-2 | 1 | 100 | 20 | 10 | 5 | 145 |

<Sensitivity Evaluation>

Each composition was spin-coated on a silicon wafer substrate and dried by heating at 110° C. for three minutes using a hot plate, thereby preparing a resin film having a thickness of about 20 μm. Then, pattern exposure (i-rays) was performed using TME-150RSC (TOPCON CORPORATION), followed by post-exposure baking (PEB) using a hot plate at 110° C. for three minutes. Subsequently, development was performed for two minutes by an immersion method using a 2.38% by weight aqueous solution of tetramethyl ammonium hydroxide. The workpiece was washed with running water and then subjected to nitrogen blowing, thereby forming a 10 μm line-and-space pattern. Next, a minimum required exposure dose (corresponding to sensitivity) to form a pattern having a film-remaining ratio of 95% or higher was measured. The film remaining ratio refers to a ratio of the remaining film after development relative to that before development.

<Storage Stability Evaluation>

The photosensitivity (sensitivity) of the chemically amplifiable negative resist composition immediately after preparation and the photosensitivity after one month storage at 40° C. were analyzed as above. The storage stability was evaluated based on the following criteria.
Good (○): The difference between the sensitivity after one month storage at 40° C. and the sensitivity immediately after preparation is less than 5%.
Bad (x): The difference between the sensitivity after one month storage at 40° C. and the sensitivity immediately after preparation is 5% or more.

<Pattern Shape Evaluation>

The cross-sectional shape of the 20 μm-thick L&S pattern formed on the silicon wafer substrate by the above operation was observed with a scanning electron microscope to measure the length La of the lower side and the length Lb of the upper side. The pattern shape was evaluated based on the following criteria. Table 6 shows the results.
Very good (○○): 0.90≤La/Lb≤1
Good (○): 0.85≤La/Lb<0.90
Bad (x): La/Lb<0.85

TABLE 6

| Example | Example of corresponding photoacid generator (E) | Minimum required exposure dose (mJ/cm$^2$) | Storage stability | Pattern shape |
|---|---|---|---|---|
| N1 | Example 1 | 140 | ○ | ○ |
| N2 | Example 2 | 120 | ○ | ○ |
| N3 | Example 3 | 120 | ○ | ○ |
| N4 | Example 5 | 110 | ○ | ○ |
| N5 | Example 6 | 110 | ○ | ○ |
| N6 | Example 8 | 110 | ○ | ○ |
| N7 | Example 9 | 140 | ○ | ○ |
| N8 | Example 10 | 120 | ○ | ○ |
| N9 | Example 11 | 120 | ○ | ○ |
| N10 | Example 13 | 110 | ○ | ○ |
| N11 | Example 14 | 110 | ○ | ○ |
| N12 | Example 16 | 110 | ○ | ○ |
| N13 | Example 17 | 130 | ○ | ○ |
| N14 | Example 18 | 110 | ○ | ○ |
| N15 | Example 19 | 110 | ○ | ○ |
| N16 | Example 21 | 100 | ○ | ○ |
| N17 | Example 22 | 100 | ○ | ○ |
| N18 | Example 24 | 100 | ○ | ○ |
| N19 | Example 25 | 120 | ○ | ○ |
| N20 | Example 26 | 100 | ○ | ○ |
| N21 | Example 27 | 100 | ○ | ○ |
| N22 | Example 29 | 100 | ○ | ○ |
| N23 | Example 30 | 100 | ○ | ○ |
| N24 | Example 32 | 100 | ○ | ○ |
| N25 | Example 33 | 120 | ○ | ○ |
| N26 | Example 34 | 100 | ○ | ○ |
| N27 | Example 35 | 100 | ○ | ○ |
| N28 | Example 37 | 100 | ○ | ○ |
| N29 | Example 38 | 100 | ○ | ○ |
| N30 | Example 40 | 100 | ○ | ○ |
| N31 | Example 41 | 120 | ○ | ○ |
| N32 | Example 42 | 100 | ○ | ○ |
| N33 | Example 43 | 100 | ○ | ○ |
| N34 | Example 45 | 100 | ○ | ○ |
| N35 | Example 46 | 100 | ○ | ○ |
| N36 | Example 48 | 100 | ○ | ○ |
| N37 | Example 49 | 100 | ○ | ○ |
| N38 | Example 50 | 100 | ○ | ○ |
| N39 | Example 51 | 100 | ○ | ○ |
| Comparative Example | | | | |
| HN1 | Comparative Example 1 | 190 | ○ | ○ |
| HN2 | Comparative Example 3 | 170 | ○ | ○ |
| HN3 | Ref-1 | 850 | ○ | ○ |
| HN4 | Ref-2 | 3000 or more | — | — |

Note)
—: The storage stability was not evaluated because the minimum required exposure dose could not be specified.

As demonstrated in Table 6, the minimum required exposure doses for the chemically amplifiable negative photoresist compositions of Examples N1 to N39 are lower than those of Comparative Examples HN1 to HN4. Specifically, the photoacid generators of the present invention have a higher sensitivity than the comparative photoacid generators and are also excellent in storage stability and pattern shapes. When the substituent R5 is bulkier or the number n of R5 is larger in the formula (1), better photosensitivity is exhibited, and the corresponding negative photoresist compositions have a higher sensitivity.

[Evaluation of Solubility in Solvent and Cationically Polymerizable Compound]

<Evaluation of Solubility in Solvent>

The sulfonium salt of the present invention was put in a solvent-3 (γ-butyrolactone) or a solvent-4 (propylene carbonate), and the highest concentration (solubility, unit: weight percent, wt %) to which the salt was completely dissolved at room temperature (25° C.) was determined.

<Evaluation of Solubility in Cationically Polymerizable Compound>

The sulfonium salt of the present invention in an amount of 5 wt % was put in a cationically polymerizable compound which was a monomer-1 (3,4-epoxycyclohexylmethyl-3,4-epoxycyclohexane carboxylate, Daicel Corporation, Celloxide 2021P) or a monomer-2 (cyclohexane dimethanol divinyl ether, Nippon Carbide Industries Co., Inc., CHDVE) and then heated to 60° C. The appearance after heating was evaluated based on the following criteria. Table 7 shows the results.

(Evaluation Criteria)
Good (○): Uniformly dissolved
Fair (Δ): Slightly suspended
Bad (x): Mostly suspended, or phase separation occurred As demonstrated in Table 7, the sulfonium salts of the present invention have a higher solubility in solvents and cationically polymerizable compounds than the sulfonium salts of the comparative examples. The solubility varies depending on the structures of the cations and the anions. Based on comparison with the same counter anion, when the substituent R5 is bulkier in the formula (1), better solubility tends to be exhibited, and when the number n of R5 is larger, much better solubility is exhibited.

INDUSTRIAL APPLICABILITY

The sulfonium salt of the present invention is suitable as a photoacid generator for use in paints, coating agents, various coating materials (e.g., hard coats, anti-fouling coating materials, anti-fogging coating materials, anti-corrosion coating materials, optical fibers), back surface treatment agents for adhesive tapes, release coating materials of release sheets (e.g., release papers, release plastic films, release metal foils) for adhesive labels, printing plates, dental materials (dental formulations, dental composites), ink compositions, inkjet ink compositions, positive resists (for formation of connection terminals and wiring patterns in production of electronic components such as circuit boards, CSP, and MEMS elements), resist films, liquid resists, negative resists (e.g., permanent film materials of surface protecting films, interlayer dielectric films, or planarizing films for semiconductor elements and the like), resists for MEMS, positive photosensitive materials, negative photosensitive materials, various adhesives (e.g., various temporary fixing agents for electronic components, adhesives for HDD, adhesives for pick-up lenses, adhesives for functional films for FPD (e.g., polarizing plates, antireflection films), holographic resins, FPD materials (e.g., color filters, black

TABLE 7

|  | Example of corresponding photoacid generator | Counter anion (X$^-$) | Solubility (wt %) | | | |
| --- | --- | --- | --- | --- | --- | --- |
|  |  |  | Solvent-3 | Solvent-4 | Monomer-1 | Monomer-2 |
| Example |  |  |  |  |  |  |
| S1 | Example 4 | PF$_6^-$ | 12 | 12 | ○ | Δ |
| S2 | Example 12 |  | 10 | 21 | ○ | Δ |
| S3 | Example 20 |  | 25 | 27 | ○ | ○ |
| S4 | Example 28 |  | 30 | 25 | ○ | ○ |
| S5 | Example 36 |  | 25 | 25 | ○ | ○ |
| S6 | Example 44 |  | 33 | 31 | ○ | ○ |
| S7 | Example 6 | PF$_3$(C$_2$F$_5$)$_3^-$ | 23 | 32 | ○ | ○ |
| S8 | Example 14 |  | 31 | 32 | ○ | ○ |
| S9 | Example 22 |  | 38 | 33 | ○ | ○ |
| S10 | Example 30 |  | 40 | 33 | ○ | ○ |
| S11 | Example 38 |  | 40 | 33 | ○ | ○ |
| S12 | Example 46 |  | 49 | 33 | ○ | ○ |
| S13 | Example 49 |  | 45 | 38 | ○ | ○ |
| S14 | Example 50 |  | 40 | 30 | ○ | ○ |
| S15 | Example 51 |  | 40 | 32 | ○ | ○ |
| S16 | Example 7 | SbF$_6^-$ | 15 | 15 | ○ | Δ |
| S17 | Example 15 |  | 18 | 20 | ○ | Δ |
| S18 | Example 23 |  | 25 | 24 | ○ | ○ |
| S19 | Example 31 |  | 25 | 23 | ○ | ○ |
| S20 | Example 39 |  | 29 | 23 | ○ | ○ |
| S21 | Example 47 |  | 33 | 30 | ○ | ○ |
| Comparative Example |  |  |  |  |  |  |
| HS1 | Comparative Example 2 | PF6$^-$ | 7 | 2 | ○ | x |
| HS2 | Comparative Example 3 | PF$_3$(C$_2$F$_5$)$_3^-$ | 23 | 32 | ○ | Δ |
| HS3 | Comparative Example 4 | SbF$_6^-$ | 9 | 3 | ○ | x |

The invention claimed is:

1. A sulfonium salt of formula (1):

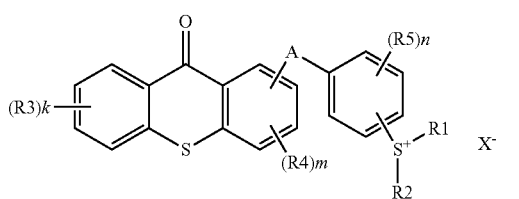

wherein R1 is a thioxanthonyl group; R2 is a phenyl group, wherein at least one hydrogen atom in the phenyl group is replaced by a substituent (t); the substituent (t) is at least one selected from the group consisting of a C1-C18 alkyl group and a C1-C18 alkoxy group; R3, R4 and R5 are each independently an alkyl group or an alkoxy group; k, m, and n respectively are the numbers of R3, R4, and R5; k is 0; m is 0; n is an integer of 1 to 4;

A is a —O— group, a —S— group, a —SO— group, a —SO$_2$— group, or a —CO— group; O is an oxygen atom; S is a sulfur atom; and X$^-$ is a monovalent polyatomic anion.

2. The sulfonium salt according to claim 1, wherein A is a —O— group or a —S— group.

3. The sulfonium salt according to claim 1, wherein n is 1 or 2, and A is a —S— group.

4. The sulfonium salt according to claim 1, wherein X$^-$ is an anion of formula MY$_a^-$, (Rf)$_b$PF$_{6-b}^-$, R$^6_c$BY$_{4-c}^-$, R$_c^6$GaY$_{4-c}^-$, R$^7$SO$_3^-$, (R$^7$SO$_2$)$_3$C$^-$, or (R$^7$SO$_2$)$_2$N$^-$, wherein M is a phosphorus atom, a boron atom, an arsenic atom, or an antimony atom; Y is a halogen atom; Rf is an alkyl group in which 80 mol % or more of hydrogen atoms are replaced by fluorine atoms; P is a phosphorus atom; F is a fluorine atom; R$^6$ is a phenyl group in which at least one hydrogen atom is replaced by a halogen atom, a trifluoromethyl group, a nitro group, or a cyano group; B is a boron atom; Ga is a gallium atom; R$^7$ is a C1-C20 alkyl group, a C1-C20 perfluoroalkyl group, or a C6-C20 aryl group; S is a sulfur atom; O is an oxygen atom; C is a carbon atom; N is a nitrogen atom; a is an integer of 4 to 6; b is an integer of 1 to 5; and c is an integer of ) 1 to 4.

5. The sulfonium salt according to claim 1, wherein X$^-$ is an anion of formula SbF$_6^-$, an anion of formula PF$_6^-$, an anion of formula BF$_4^-$, an anion of formula (CF$_3$CF$_2$)$_3$PF$_3^-$, an anion of formula (CF$_3$CF$_2$CF$_2$CF$_2$)$_3$PF$_3^-$, an anion of formula (C$_6$F$_5$)$_4$B$^-$, an anion of formula (C$_6$H$_5$)(C$_6$F$_5$)$_3$B$^-$, an anion of formula ((CF$_3$)$_2$C$_6$H$_3$)$_4$B$^-$, an anion of formula (C$_6$F$_5$)$_4$Ga$^-$, an anion of formula ((CF$_3$)$_2$C$_6$H$_3$)$_4$Ga$^-$, a trifluoromethanesulfonic acid anion, a nonafluorobutanesulfonic acid anion, a methanesulfonic acid anion, a camphor sulfonic acid anion, a benzenesulfonic acid anion, or a p-toluenesulfonic acid anion.

6. The sulfonium salt according to claim 1, wherein R2 is a phenyl group, wherein one or two hydrogen atoms are replaced by the substituent (t).

7. A photoacid generator comprising the sulfonium salt according to claim 1.

8. An energy ray-curable composition comprising the photoacid generator according to claim 7 and a cationically polymerizable compound.

9. A cured product obtainable by curing the energy ray-curable composition according to claim 8.

10. A chemically amplifiable positive photoresist composition, comprising:
a component (A) comprising the photoacid generator according to claim 7; and
a component (B) that is a resin whose solubility in alkali is increased by the action of an acid.

11. The chemically amplifiable positive photoresist composition according to claim 10,
wherein the component (B) that is a resin whose solubility in alkali is increased by the action of an acid comprises at least one resin selected from the group consisting of a novolac resin (B1), a polyhydroxystyrene resin (B2), and an acrylic resin (B3).

12. The chemically amplifiable positive photoresist composition according to claim 10, further comprising an alkali soluble resin (C) and an acid diffusion control agent (D).

13. A method for producing a resist pattern, comprising:
stacking a photoresist layer comprising the chemically amplifiable positive photoresist composition according to claim 10 and having a thickness of 5 to 150 μum on a support to form a photoresist laminate;
exposing site-selectively the photoresist laminate to light or radiation; and
developing the photoresist laminate after the exposure to give a resist pattern.

14. A chemically amplifiable negative photoresist composition, comprising:
a component (E) comprising the photoacid generator according to claim 7;
a component (F) that is an alkali soluble resin having a phenolic hydroxy group; and
a crosslinking agent (G).

15. The chemically amplifiable negative photoresist composition according to claim 14, further comprising crosslinked fine particles (H).

16. A cured product obtainable by curing the chemically amplifiable negative photoresist composition according to claim 14.

* * * * *